US009353382B2

(12) United States Patent
Durocher et al.

(10) Patent No.: US 9,353,382 B2

(45) Date of Patent: May 31, 2016

(54) PROCESS, VECTORS AND ENGINEERED CELL LINES FOR ENHANCED LARGE-SCALE TRANSFECTION

(71) Applicant: National Research Council of Canada, Ottawa (CA)

(72) Inventors: Yves Durocher, Montreal (CA); Martin Loignon, Quebec (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 14/068,336

(22) Filed: Oct. 31, 2013

(65) Prior Publication Data

US 2014/0051170 A1 Feb. 20, 2014

Related U.S. Application Data

(62) Division of application No. 12/989,898, filed as application No. PCT/CA2009/000263 on Mar. 9, 2009, now Pat. No. 8,637,315.

(60) Provisional application No. 61/071,760, filed on May 15, 2008.

(51) Int. Cl.

| | |
|---|---|
| ***C12N 15/85*** | (2006.01) |
| ***A61K 38/00*** | (2006.01) |
| ***C07K 14/005*** | (2006.01) |

(52) U.S. Cl.

CPC .............. *C12N 15/85* (2013.01); *C07K 14/005* (2013.01); *C07K 2319/71* (2013.01); *C12N 2710/16222* (2013.01); *C12N 2710/16622* (2013.01); *C12N 2800/108* (2013.01); *C12N 2800/40* (2013.01)

(58) Field of Classification Search

None

See application file for complete search history.

(56) References Cited

U.S. PATENT DOCUMENTS

| | | | | |
|---|---|---|---|---|
| 5,976,807 | A | 11/1999 | Horlick et al. | |
| 6,133,025 | A | 10/2000 | Seed | |
| 6,417,002 | B1 * | 7/2002 | Horlick et al. | 435/455 |
| 6,797,494 | B1 | 9/2004 | Antoniou et al. | |
| 6,960,429 | B2 | 11/2005 | Sugden et al. | |
| 2003/0059942 | A1 | 3/2003 | Cho et al. | |
| 2005/0170450 | A1 * | 8/2005 | Durocher et al. | 435/69.1 |
| 2005/0260564 | A1 | 11/2005 | Sugden et al. | |
| 2008/0070232 | A1 * | 3/2008 | Durocher | 435/5 |

FOREIGN PATENT DOCUMENTS

| | | | | |
|---|---|---|---|---|
| WO | 2002-090533 | | 11/2002 | |
| WO | 2005-024030 | | 3/2005 | |
| WO | 2006-96989 | | 9/2006 | |
| WO | WO 2006/096989 | * | 9/2006 | A61K 39/00 |
| WO | 2007-048601 | | 5/2007 | |

OTHER PUBLICATIONS

Segura et al. (Biotechnology and Bioengineering, Nov. 2007, vol. 98, p. 789-799).*

Durocher et al. (Nucleic Acids Research, 2002, p. 1-9).*

Extended European Search Report of Oct. 17, 2011 on European application 09745326.0.

Elham Ettehadieh et al: Cytotechnology, vol. 38, No. 1/3, Jan. 1, 2002, pp. 11-14.

Gaurav Backliwal et al: Valproic acid: A viable alternative to sodium butyrate for enhancing protein expression in mammalian cell cultures. Biotechnology and Biotechology and Bioengineering, vol. 101, No. 1, Mar. 7, 2008, pp. 182-189.

Kostrouchov M. et al: Valproic acid, a molecular lead to multiple regulatory pathways. Folia Biologica, vol. 53, No. 2, Jan. 1, 2007, pp. 37-49.

ISR and Written Opinion on International Patent Application PCT-CA2009-000263, Jun. 26, 2009.

Boussif et al. Gene Therapy. (1996) 3. 1074-1080.

Sheng et al. Molecular and Cellular Biology. (2005) 9419-9426.

Phiel et al. The Journal of Biological Chemistry. (2001) 276(39), 36734-36741.

Kishida et al. Journal of Biotechnology. (2008) 133,201-207.

Durocher et al. Analytical Biochemistry. (2000) 284, 316-326.

Tomiyasu et al. Biochemical and Biophysical Research Communications. (1998) 253, 733-738.

Thomas et al. PNAS. (2005) 102(16), 5679-5684.

Sears et al. Journal of Virology. (2003) 77(21), 11767-11780.

Mizuguchi et al. FEBS Letters. (2000) 472, 173-178.

Krysan et al. Gene. (1993) 137-143.

Kennedy et al. Mol Cell Bioi. (2003) 23(19), 6901-6908.

Kang et al. Proc Nail Acad Sci USA. (2001) 98(26). 15233-15238.

Chen et al. Mol Cancer. (2006) 5,71.

Office Action issued by the Canadian Patent Office with respect to corresponding Canadian Application No. 2,722,835.

* cited by examiner

*Primary Examiner* — Agnieszka Boesen

(74) *Attorney, Agent, or Firm* — Sonia Patenaude

(57) ABSTRACT

Processes, vectors and engineered cell lines for large-scale transfection and protein production in mammalian cells, especially Chinese Hamster Ovary (CHO) cells are described in which transfection efficiencies are realized through the use of a single vector system, the use of functional oriP sequences in all plasmids, the use of codon-optimized Epstein-Barr virus nuclear antigen-1 (EBNA1) constructs, the use of a fusion protein between a truncated Epstein-Barr virus nuclear antigen-1c (EBNA1c) protein and a herpes simplex virus protein VP16, the use of a 40 kDa fully deacetylated poly (ethylenimine) as a transfection reagent, the use of co-expression of a fibroblast growth factor (FGF) and/or the use of protein kinase B to potentiate heterologous gene expression enhancement by valproic acid (VPA).

14 Claims, 10 Drawing Sheets

A

CHO CTRL

Bulk 2 dpt

Bulk 16 dpt

Clone 3E7

B

SEQUENCE LISTING

```
<160> NUMBER OF SEQ ID NOS: 15

<210> SEQ ID NO 1
<211> LENGTH: 641
<212> TYPE: PRT
<213> ORGANISM: Artificial Sequence
<220> FEATURE:
<223> OTHER INFORMATION: Epstein Barr Virus EBNA1s Truncated Protein

<400> SEQUENCE: 1

Met Ser Asp Glu Gly Pro Gly Thr Gly Pro Gly Asn Gly Leu Gly Glu
1               5                   10                  15
```

```
Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Gly Ala Gly Ala Gly
            100                 105                 110

Gly Gly Ala Gly Gly Ala Gly Gly Ala Gly Gly Ala Gly Ala Gly Gly
        115                 120                 125

Gly Ala Gly Ala Gly Gly Gly Ala Gly Gly Ala Gly Gly Ala Gly Ala
    130                 135                 140

Gly Gly Gly Ala Gly Ala Gly Gly Gly Ala Gly Gly Ala Gly Ala Gly
145                 150                 155                 160

Gly Gly Ala Gly Gly Ala Gly Gly Ala Gly Ala Gly Gly Gly Ala Gly
                165                 170                 175

Ala Gly Gly Gly Ala Gly Gly Ala Gly Ala Gly Gly Gly Ala Gly Gly
            180                 185                 190

Ala Gly Gly Ala Gly Ala Gly Gly Gly Ala Gly Ala Gly Gly Ala Gly
        195                 200                 205

Gly Ala Gly Gly Ala Gly Ala Gly Gly Ala Gly Ala Gly Gly Gly Ala
    210                 215                 220

Gly Gly Ala Gly Gly Ala Gly Ala Gly Gly Ala Gly Ala Gly Gly Ala
225                 230                 235                 240

Gly Ala Gly Gly Ala Gly Ala Gly Gly Ala Gly Gly Ala Gly Ala Gly
                245                 250                 255

Gly Ala Gly Gly Ala Gly Ala Gly Gly Ala Gly Gly Ala Gly Ala Gly
            260                 265                 270

Gly Gly Ala Gly Gly Ala Gly Ala Gly Gly Gly Ala Gly Gly Ala Gly
        275                 280                 285

Ala Gly Gly Ala Gly Gly Ala Gly Ala Gly Gly Ala Gly Gly Ala Gly
    290                 295                 300

Ala Gly Gly Ala Gly Gly Ala Gly Ala Gly Gly Gly Ala Gly Ala Gly
305                 310                 315                 320

Gly Ala Gly Ala Gly Gly Gly Gly Arg Gly Arg Gly Gly Ser Gly Gly
                325                 330                 335

Arg Gly Arg Gly Gly Ser Gly Gly Arg Gly Arg Gly Gly Ser Gly Gly
            340                 345                 350

Arg Arg Gly Arg Gly Arg Glu Arg Ala Arg Gly Gly Ser Arg Glu Arg
        355                 360                 365

Ala Arg Gly Arg Gly Arg Gly Arg Gly Glu Lys Arg Pro Arg Ser Pro
    370                 375                 380

Ser Ser Gln Ser Ser Ser Ser Gly Ser Pro Pro Arg Arg Pro Pro Pro
385                 390                 395                 400

Gly Arg Arg Pro Phe Phe His Pro Val Gly Glu Ala Asp Tyr Phe Glu
                405                 410                 415

Tyr His Gln Glu Gly Gly Pro Asp Gly Glu Pro Asp Val Pro Pro Gly
            420                 425                 430
```

```
Ala Ile Glu Gln Gly Pro Ala Asp Asp Pro Gly Glu Gly Pro Ser Thr
        435                 440                 445

Gly Pro Arg Gly Gln Gly Asp Gly Gly Arg Arg Lys Lys Gly Gly Trp
    450                 455                 460

Phe Gly Lys His Arg Gly Gln Gly Gly Ser Asn Pro Lys Phe Glu Asn
465                 470                 475                 480

Ile Ala Glu Gly Leu Arg Ala Leu Leu Ala Arg Ser His Val Glu Arg
                485                 490                 495

Thr Thr Asp Glu Gly Thr Trp Val Ala Gly Val Phe Val Tyr Gly Gly
            500                 505                 510

Ser Lys Thr Ser Leu Tyr Asn Leu Arg Arg Gly Thr Ala Leu Ala Ile
        515                 520                 525

Pro Gln Cys Arg Leu Thr Pro Leu Ser Arg Leu Pro Phe Gly Met Ala
    530                 535                 540

Pro Gly Pro Gly Pro Gln Pro Gly Pro Leu Arg Glu Ser Ile Val Cys
545                 550                 555                 560

Tyr Phe Met Val Phe Leu Gln Thr His Ile Phe Ala Glu Val Leu Lys
                565                 570                 575

Asp Ala Ile Lys Asp Leu Val Met Thr Lys Pro Ala Pro Thr Cys Asn
            580                 585                 590

Ile Arg Val Thr Val Cys Ser Phe Asp Asp Gly Val Asp Leu Pro Pro
        595                 600                 605

Trp Phe Pro Pro Met Val Glu Gly Ala Ala Ala Glu Gly Asp Asp Gly
    610                 615                 620

Asp Asp Gly Asp Glu Gly Gly Asp Gly Asp Glu Gly Glu Glu Gly Gln
625                 630                 635                 640

Glu


<210> SEQ ID NO 2
<211> LENGTH: 417
<212> TYPE: PRT
<213> ORGANISM: Artificial Sequence
<220> FEATURE:
<223> OTHER INFORMATION: Epstein Barr Virus EBNA1t Truncated Protein

<400> SEQUENCE: 2

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Gly Gly Arg Gly Arg Gly Gly Ser Gly Gly
            100                 105                 110

Arg Gly Arg Gly Gly Ser Gly Gly Arg Gly Arg Gly Gly Ser Gly Gly
        115                 120                 125

Arg Arg Gly Arg Gly Arg Glu Arg Ala Arg Gly Gly Ser Arg Glu Arg
    130                 135                 140

Ala Arg Gly Arg Gly Arg Gly Arg Gly Glu Lys Arg Pro Arg Ser Pro
```

-continued

```
145                 150                 155                 160

Ser Ser Gln Ser Ser Ser Ser Gly Ser Pro Pro Arg Arg Pro Pro Pro
                165                 170                 175

Gly Arg Arg Pro Phe Phe His Pro Val Gly Glu Ala Asp Tyr Phe Glu
            180                 185                 190

Tyr His Gln Glu Gly Gly Pro Asp Gly Glu Pro Asp Val Pro Pro Gly
        195                 200                 205

Ala Ile Glu Gln Gly Pro Ala Asp Asp Pro Gly Glu Gly Pro Ser Thr
    210                 215                 220

Gly Pro Arg Gly Gln Gly Asp Gly Gly Arg Arg Lys Lys Gly Gly Trp
225                 230                 235                 240

Phe Gly Lys His Arg Gly Gln Gly Gly Ser Asn Pro Lys Phe Glu Asn
                245                 250                 255

Ile Ala Glu Gly Leu Arg Ala Leu Leu Ala Arg Ser His Val Glu Arg
            260                 265                 270

Thr Thr Asp Glu Gly Thr Trp Val Ala Gly Val Phe Val Tyr Gly Gly
        275                 280                 285

Ser Lys Thr Ser Leu Tyr Asn Leu Arg Arg Gly Thr Ala Leu Ala Ile
    290                 295                 300

Pro Gln Cys Arg Leu Thr Pro Leu Ser Arg Leu Pro Phe Gly Met Ala
305                 310                 315                 320

Pro Gly Pro Gly Pro Gln Pro Gly Pro Leu Arg Glu Ser Ile Val Cys
                325                 330                 335

Tyr Phe Met Val Phe Leu Gln Thr His Ile Phe Ala Glu Val Leu Lys
            340                 345                 350

Asp Ala Ile Lys Asp Leu Val Met Thr Lys Pro Ala Pro Thr Cys Asn
        355                 360                 365

Ile Arg Val Thr Val Cys Ser Phe Asp Asp Gly Val Asp Leu Pro Pro
    370                 375                 380

Trp Phe Pro Pro Met Val Glu Gly Ala Ala Ala Glu Gly Asp Asp Gly
385                 390                 395                 400

Asp Asp Gly Asp Glu Gly Gly Asp Gly Asp Glu Gly Glu Glu Gly Gln
                405                 410                 415

Glu


<210> SEQ ID NO 3
<211> LENGTH: 306
<212> TYPE: PRT
<213> ORGANISM: Artificial Sequence
<220> FEATURE:
<223> OTHER INFORMATION: Epstein Barr Virus EBNA1c Truncated Protein

<400> SEQUENCE: 3

Met Arg Gly Arg Gly Gly Ser Gly Gly Arg Gly Arg Gly Gly Ser Gly
1               5                   10                  15

Gly Arg Arg Gly Arg Gly Arg Glu Arg Ala Arg Gly Gly Ser Arg Glu
            20                  25                  30

Arg Ala Arg Gly Arg Gly Arg Gly Arg Gly Glu Lys Arg Pro Arg Ser
        35                  40                  45

Pro Ser Ser Gln Ser Ser Ser Ser Gly Ser Pro Pro Arg Arg Pro Pro
    50                  55                  60

Pro Gly Arg Arg Pro Phe Phe His Pro Val Gly Glu Ala Asp Tyr Phe
65                  70                  75                  80

Glu Tyr His Gln Glu Gly Gly Pro Asp Gly Glu Pro Asp Val Pro Pro
                85                  90                  95
```

```
Gly Ala Ile Glu Gln Gly Pro Ala Asp Asp Pro Gly Glu Gly Pro Ser
            100                 105                 110

Thr Gly Pro Arg Gly Gln Gly Asp Gly Gly Arg Arg Lys Lys Gly Gly
        115                 120                 125

Trp Phe Gly Lys His Arg Gly Gln Gly Gly Ser Asn Pro Lys Phe Glu
    130                 135                 140

Asn Ile Ala Glu Gly Leu Arg Ala Leu Leu Ala Arg Ser His Val Glu
145                 150                 155                 160

Arg Thr Thr Asp Glu Gly Thr Trp Val Ala Gly Val Phe Val Tyr Gly
                165                 170                 175

Gly Ser Lys Thr Ser Leu Tyr Asn Leu Arg Arg Gly Thr Ala Leu Ala
            180                 185                 190

Ile Pro Gln Cys Arg Leu Thr Pro Leu Ser Arg Leu Pro Phe Gly Met
        195                 200                 205

Ala Pro Gly Pro Gly Pro Gln Pro Gly Pro Leu Arg Glu Ser Ile Val
    210                 215                 220

Cys Tyr Phe Met Val Phe Leu Gln Thr His Ile Phe Ala Glu Val Leu
225                 230                 235                 240

Lys Asp Ala Ile Lys Asp Leu Val Met Thr Lys Pro Ala Pro Thr Cys
                245                 250                 255

Asn Ile Arg Val Thr Val Cys Ser Phe Asp Asp Gly Val Asp Leu Pro
            260                 265                 270

Pro Trp Phe Pro Pro Met Val Glu Gly Ala Ala Ala Glu Gly Asp Asp
        275                 280                 285

Gly Asp Asp Gly Asp Glu Gly Gly Asp Gly Asp Glu Gly Glu Glu Gly
    290                 295                 300

Gln Glu
305
```

```
<210> SEQ ID NO 4
<211> LENGTH: 337
<212> TYPE: PRT
<213> ORGANISM: Artificial Sequence
<220> FEATURE:
<223> OTHER INFORMATION: Epstein Barr Virus EBNA1s Truncated Protein

<400> SEQUENCE: 4

Met Arg Arg Gly Gly Asp Asn His Gly Arg Gly Arg Gly Arg Gly Arg
1               5                   10                  15

Gly Arg Gly Gly Gly Arg Pro Gly Ala Pro Gly Gly Ser Gly Ser Gly
            20                  25                  30

Pro Arg His Arg Asp Gly Val Arg Arg Pro Gln Lys Arg Pro Ser Cys
        35                  40                  45

Ile Gly Cys Lys Gly Thr His Gly Gly Thr Gly Ala Gly Ala Gly Ala
    50                  55                  60

Gly Gly Ala Gly Ala Gly Gly Gly Gly Glu Lys Arg Pro Arg Ser Pro
65                  70                  75                  80

Ser Ser Gln Ser Ser Ser Ser Gly Ser Pro Pro Arg Arg Pro Pro Pro
                85                  90                  95

Gly Arg Arg Pro Phe Phe His Pro Val Gly Glu Ala Asp Tyr Phe Glu
            100                 105                 110

Tyr His Gln Glu Gly Gly Pro Asp Gly Glu Pro Asp Val Pro Pro Gly
        115                 120                 125

Ala Ile Glu Gln Gly Pro Ala Asp Asp Pro Gly Glu Gly Pro Ser Thr
    130                 135                 140
```

```
Gly Pro Arg Gly Gln Gly Asp Gly Gly Arg Arg Lys Lys Gly Gly Trp
145                 150                 155                 160

Phe Gly Lys His Arg Gly Gln Gly Gly Ser Asn Pro Lys Phe Glu Asn
                165                 170                 175

Ile Ala Glu Gly Leu Arg Ala Leu Leu Ala Arg Ser His Val Glu Arg
            180                 185                 190

Thr Thr Asp Glu Gly Thr Trp Val Ala Gly Val Phe Val Tyr Gly Gly
        195                 200                 205

Ser Lys Thr Ser Leu Tyr Asn Leu Arg Arg Gly Thr Ala Leu Ala Ile
    210                 215                 220

Pro Gln Cys Arg Leu Thr Pro Leu Ser Arg Leu Pro Phe Gly Met Ala
225                 230                 235                 240

Pro Gly Pro Gly Pro Gln Pro Gly Pro Leu Arg Glu Ser Ile Val Cys
                245                 250                 255

Tyr Phe Met Val Phe Leu Gln Thr His Ile Phe Ala Glu Val Leu Lys
            260                 265                 270

Asp Ala Ile Lys Asp Leu Val Met Thr Lys Pro Ala Pro Thr Cys Asn
        275                 280                 285

Ile Arg Val Thr Val Cys Ser Phe Asp Asp Gly Val Asp Leu Pro Pro
    290                 295                 300

Trp Phe Pro Pro Met Val Glu Gly Ala Ala Ala Glu Gly Asp Asp Gly
305                 310                 315                 320

Asp Asp Gly Asp Glu Gly Gly Asp Gly Asp Glu Gly Glu Glu Gly Gln
                325                 330                 335

Glu
```

<210> SEQ ID NO 5
<211> LENGTH: 1926
<212> TYPE: DNA
<213> ORGANISM: Artificial Sequence
<220> FEATURE:
<223> OTHER INFORMATION: Epstein Barr Virus EBNA1 Full Length cDNA

<400> SEQUENCE: 5

```
atgtctgacg aggggccagg tacaggacct ggaaatggcc taggagagaa gggagacaca      60

tctggaccag aaggctccgg cggcagtgga cctcaaagaa gagggggtga taaccatgga     120

cgaggacggg gaagaggacg aggacgagga ggcggaagac caggagcccc gggcggctca     180

ggatcagggc caagacatag agatggtgtc cggagacccc aaaaacgtcc aagttgcatt     240

ggctgcaaag ggacccacgg tggaacagga gcaggagcag gagcgggagg ggcaggagca     300

ggaggggcag gagcaggagg aggggcagga gcaggaggag ggcaggaggg gcaggagggg     360

gcaggagggg caggagcagg aggaggggca ggagcaggag gaggggcagg aggggcagga     420

ggggcaggag caggaggagg ggcaggagca ggaggagggg caggaggggc aggagcagga     480

ggaggggcag gaggggcagg aggggcagga gcaggaggag ggcaggagc aggaggaggg      540

gcaggagggg caggagcagg aggaggggca ggaggggcag gaggggcagg agcaggagga     600

ggggcaggag caggaggggc aggaggggca ggaggggcag gagcaggagg ggcaggagca     660

ggaggagggg caggaggggc aggaggggca ggagcaggag ggcaggagc aggaggggca      720

ggagcaggag ggcaggagc aggaggggca ggaggggcag gagcaggagg ggcaggaggg      780

gcaggagcag gaggggcagg aggggcagga gcaggaggag ggcaggagg ggcaggagca      840

ggaggagggg caggaggggc aggagcagga ggggcaggag ggcaggagc aggaggggca      900
```

```
ggaggggcag gagcaggagg ggcaggaggg gcaggagcag gaggaggggc aggagcagga    960

ggggcaggag caggaggtgg aggccggggt cgaggaggca gtggaggccg ggtcgagga    1020

ggtagtggag gccggggtcg aggaggtagt ggaggccgcc ggggtagagg acgtgaaaga   1080

gccagggggg gaagtcgtga aagagccagg gggagaggtc gtggacgtgg agaaaagagg   1140

cccaggagtc ccagtagtca gtcatcatca tccgggtctc caccgcgcag gccccctcca   1200

ggtagaaggc catttttcca ccctgtaggg gaagccgatt attttgaata ccaccaagaa   1260

ggtggcccag atggtgagcc tgacgtgccc ccgggagcga tagagcaggg ccccgcagat   1320

gacccaggag aaggcccaag cactggaccc cggggtcagg gtgatggagg caggcgcaaa   1380

aaaggagggt ggtttggaaa gcatcgtggt caaggaggtt ccaacccgaa atttgagaac   1440

attgcagaag gtttaagagc tctcctggct aggagtcacg tagaaaggac taccgacgaa   1500

ggaacttggg tcgccggtgt gttcgtatat ggaggtagta agacctccct ttacaaccta   1560

aggcgaggaa ctgcccttgc tattccacaa tgtcgtctta caccattgag tcgtctcccc   1620

tttggaatgg cccctggacc cggcccacaa cctggcccgc taagggagtc cattgtctgt   1680

tatttcatgg tctttttaca aactcatata tttgctgagg ttttgaagga tgcgattaag   1740

gaccttgtta tgacaaagcc cgctcctacc tgcaatatca gggtgactgt gtgcagcttt   1800

gacgatggag tagatttgcc tccctggttt ccacctatgg tggaaggggc tgccgcggag   1860

ggtgatgacg gagatgacgg agatgaagga ggtgatggag atgagggtga ggaagggcag   1920

gagtga                                                              1926
```

<210> SEQ ID NO 6
<211> LENGTH: 1254
<212> TYPE: DNA
<213> ORGANISM: Artificial Sequence
<220> FEATURE:
<223> OTHER INFORMATION: Epstein Barr Virus EBNA1t Truncated cDNA

<400> SEQUENCE: 6

```
atgtctgacg aggggccagg tacaggacct ggaaatggcc taggagagaa gggagacaca     60

tctggaccag aaggctccgg cggcagtgga cctcaaagaa gagggggtga taaccatgga    120

cgaggacggg gaagaggacg aggacgagga ggcggaagac caggagcccc gggcggctca    180

ggatcagggc caagacatag agatggtgtc cggagacccc aaaaacgtcc aagttgcatt    240

ggctgcaaag ggacccacgg tggaacagga gcaggagcag gagcgggagg ggcaggagca    300

ggaggtggag gccggggtcg aggaggcagt ggaggccggg gtcgaggagg tagtggaggc    360

cggggtcgag gaggtagtgg aggccgccgg ggtagaggac gtgaaagagc caggggggga    420

agtcgtgaaa gagccagggg gagaggtcgt ggacgtggag aaaagaggcc caggagtccc    480

agtagtcagt catcatcatc cgggtctcca ccgcgcaggc cccctccagg tagaaggcca    540

tttttccacc ctgtagggga agccgattat tttgaatacc accaagaagg tggcccagat    600

ggtgagcctg acgtgccccc gggagcgata gagcagggcc ccgcagatga cccaggagaa    660

ggcccaagca ctggaccccg gggtcagggt gatggaggca ggcgcaaaaa aggagggtgg    720

tttggaaagc atcgtggtca aggaggttcc aacccgaaat ttgagaacat tgcagaaggt    780

ttaagagctc tcctggctag gagtcacgta gaaaggacta ccgacgaagg aacttgggtc    840

gccggtgtgt tcgtatatgg aggtagtaag acctcccttt acaacctaag gcgaggaact    900

gcccttgcta ttccacaatg tcgtcttaca ccattgagtc gtctcccctt tggaatggcc    960

cctggacccg gcccacaacc tggcccgcta agggagtcca ttgtctgtta tttcatggtc   1020
```

```
tttttacaaa ctcatatatt tgctgaggtt ttgaaggatg cgattaagga ccttgttatg   1080

acaaagcccg ctcctacctg caatatcagg gtgactgtgt gcagctttga cgatggagta   1140

gatttgcctc cctggtttcc acctatggtg gaaggggctg ccgcggaggg tgatgacgga   1200

gatgacggag atgaaggagg tgatggagat gagggtgagg aagggcagga gtga         1254
```

<210> SEQ ID NO 7
<211> LENGTH: 921
<212> TYPE: DNA
<213> ORGANISM: Artificial Sequence
<220> FEATURE:
<223> OTHER INFORMATION: Epstein Barr Virus EBNA1c Truncated cDNA

<400> SEQUENCE: 7

```
atgcggggtc gaggaggtag tggaggccgg ggtcgaggag gtagtggagg ccgccggggt     60

agaggacgtg aaagagccag gggggaagt cgtgaaaagag ccaggggggag aggtcgtgga    120

cgtggagaaa agaggcccag gagtcccagt agtcagtcat catcatccgg gtctccaccg    180

cgcaggcccc ctccaggtag aaggccattt ttccaccctg taggggaagc cgattatttt    240

gaataccacc aagaaggtgg cccagatggt gagcctgacg tgcccccggg agcgatagag    300

cagggccccg cagatgaccc aggagaaggc ccaagcactg gaccccgggg tcagggtgat    360

ggaggcaggc gcaaaaaagg agggtggttt ggaaagcatc gtggtcaagg aggttccaac    420

ccgaaatttg agaacattgc agaaggttta agagctctcc tggctaggag tcacgtagaa    480

aggactaccg acgaaggaac ttgggtcgcc ggtgtgttcg tatatggagg tagtaagacc    540

tccctttaca acctaaggcg aggaactgcc cttgctattc cacaatgtcg tcttacacca    600

ttgagtcgtc tcccctttgg aatggcccct ggacccggcc cacaacctgg cccgctaagg    660

gagtccattg tctgttattt catggtcttt ttacaaactc atatatttgc tgaggttttg    720

aaggatgcga ttaaggacct tgttatgaca aagcccgctc ctacctgcaa tatcagggtg    780

actgtgtgca gctttgacga tggagtagat ttgcctccct ggtttccacc tatggtggaa    840

ggggctgccg cggagggtga tgacggagat gacggagatg aaggaggtga tggagatgag    900

ggtgaggaag ggcaggagtg a                                              921
```

<210> SEQ ID NO 8
<211> LENGTH: 1014
<212> TYPE: DNA
<213> ORGANISM: Artificial Sequence
<220> FEATURE:
<223> OTHER INFORMATION: Epstein Barr Virus EBNA1s Truncated cDNA

<400> SEQUENCE: 8

```
atgcggagag gcggcgacaa ccacggcagg ggcagaggcc ggggaagagg cagaggcggc     60

ggaaggcctg gcgcccctgg cggcagcggc tccggcccca gacaccggga cggcgtgcgg    120

agaccccaga agcggcccag ctgcatcggc tgcaagggca cccacggcgg cacaggcgct    180

ggcgcagggg ctggcggagc cggagccggg ggagggggcg agaagaggcc cagaagcccc    240

agcagccaga gcagcagcag cggcagcccc cccagaaggc cccctcccgg caggcggccc    300

ttcttccacc ccgtgggcga ggccgactac ttcgagtacc accaggaagg cggccctgac    360

ggcgagcccg acgtgcctcc tggcgccatc gagcagggcc ccgcagatga cccaggagaa    420

ggcccaagca ctggaccccg gggtcagggt gatggaggca ggcgcaaaaa aggagggtgg    480

tttggaaagc atcgtggtca aggaggttcc aacccgaaat ttgagaacat tgcagaaggt    540
```

```
ttaagagctc tcctggctag gagtcacgta gaaaggacta ccgacgaagg aacttgggtc    600

gccggtgtgt tcgtatatgg aggtagtaag acctcccttt acaacctaag gcgaggaact    660

gcccttgcta ttccacaatg tcgtcttaca ccattgagtc gtctcccctt tggaatggcc    720

cctggacccg gcccacaacc tggcccgcta agggagtcca ttgtctgtta tttcatggtc    780

tttttacaaa ctcatatatt tgctgaggtt ttgaaggatg cgattaagga ccttgttatg    840

acaaagcccg ctcctacctg caatatcagg gtgactgtgt gcagctttga cgatggagta    900

gatttgcctc cctggtttcc acctatggtg gaaggggctg ccgcggaggg tgatgacgga    960

gatgacggag atgaaggagg tgatggagat gagggtgagg aagggcagga gtga         1014
```

<210> SEQ ID NO 9
<211> LENGTH: 1750
<212> TYPE: DNA
<213> ORGANISM: Artificial Sequence
<220> FEATURE:
<223> OTHER INFORMATION: Epstein Barr Virus Complete oriP

<400> SEQUENCE: 9

```
gtagctaccg ataagcggac cctcaagagg gcattagcaa tagtgtttat aaggccccct     60

tgttaaccct aaacgggtag catatgcttc ccgggtagta gtatatacta tccagactaa    120

ccctaattca atagcatatg ttacccaacg ggaagcatat gctatcgaat tagggttagt    180

aaaagggtcc taaggaacag cgatatctcc caccccatga gctgtcacgg ttttatttac    240

atggggtcag gattccacga gggtagtgaa ccattttagt cacaagggca gtggctgaag    300

atcaaggagc gggcagtgaa ctctcctgaa tcttcgcctg cttcttcatt ctccttcgtt    360

tagctaatag aataactgct gagttgtgaa cagtaaggtg tatgtgaggt gctcgaaaac    420

aaggtttcag gtgacgcccc cagaataaaa tttggacggg ggttcagtg gtggcattgt    480

gctatgacac caatataacc ctcacaaacc ccttgggcaa taaatactag tgtaggaatg    540

aaacattctg aatatcttta acaatagaaa tccatggggt ggggacaagc cgtaaagact    600

ggatgtccat ctcacacgaa tttatggcta tgggcaacac ataatcctag tgcaatatga    660

tactggggtt attaagatgt gtcccaggca gggaccaaga caggtgaacc atgttgttac    720

actctatttg taacaagggg aaagagagtg gacgccgaca gcagcggact ccactggttg    780

tctctaacac ccccgaaaat taaacggggc tccacgccaa tggggcccat aaacaaagac    840

aagtggccac tctttttttt gaaattgtgg agtgggggca cgcgtcagcc cccacacgcc    900

gccctgcggt tttggactgt aaaataaggg tgtaataact tggctgattg taaccccgct    960

aaccactgcg gtcaaaccac ttgcccacaa aaccactaat ggcaccccgg ggaatacctg   1020

cataagtagg tgggcgggcc aagatagggg cgcgattgct gcgatctgga ggacaaatta   1080

cacacacttg cgcctgagcg ccaagcacag ggttgttggt cctcatattc acgaggtcgc   1140

tgagagcacg gtgggctaat gttgccatgg gtagcatata ctacccaaat atctggatag   1200

catatgctat cctaatctat atctgggtag cataggctat cctaatctat atctgggtag   1260

catatgctat cctaatctat atctgggtag tatatgctat cctaatttat atctgggtag   1320

cataggctat cctaatctat atctgggtag catatgctat cctaatctat atctgggtag   1380

tatatgctat cctaatctgt atccgggtag catatgctat cctaatagag attagggtag   1440

tatatgctat cctaatttat atctgggtag catatactac ccaaatatct ggatagcata   1500

tgctatccta atctatatct gggtagcata tgctatccta atctatatct gggtagcata   1560

ggctatccta atctatatct gggtagcata tgctatccta atctatatct gggtagtata   1620
```

tgctatccta atttatatct gggtagcata ggctatccta atctatatct gggtagcata 1680
tgctatccta atctatatct gggtagtata tgctatccta atctgtatcc gggtagcata 1740
tgctatcctc 1750

<210> SEQ ID NO 10
<211> LENGTH: 866
<212> TYPE: DNA
<213> ORGANISM: Artificial Sequence
<220> FEATURE:
<223> OTHER INFORMATION: Epstein Barr Virus Truncated oriP

<400> SEQUENCE: 10
accctaaacg ggtagcatat gcttcccggg tagtagtata tactatccag actaacccta 60
attcaatagc atatgttacc caacgggaag catatgctat cgaattaggg ttagtaaaag 120
ggtcctaagg aacagcgatg taggtgggcg ggccaagata ggggcgcgat tgctgcgatc 180
tggaggacaa attacacaca cttgcgcctg agcgccaagc acagggttgt tggtcctcat 240
attcacgagg tcgctgagag cacggtgggc taatgttgcc atgggtagca tatactaccc 300
aaatatctgg atagcatatg ctatcctaat ctatatctgg gtagcatagg ctatcctaat 360
ctatatctgg gtagcatatg ctatcctaat ctatatctgg gtagtatatg ctatcctaat 420
ttatatctgg gtagcatagg ctatcctaat ctatatctgg gtagcatatg ctatcctaat 480
ctatatctgg gtagtatatg ctatcctaat ctgtatccgg gtagcatatg ctatcctaat 540
agagattagg gtagtatatg ctatcctaat ttatatctgg gtagcatata ctacccaaat 600
atctggatag catatgctat cctaatctat atctgggtag catatgctat cctaatctat 660
atctgggtag cataggctat cctaatctat atctgggtag catatgctat cctaatctat 720
atctgggtag tatatgctat cctaatttat atctgggtag cataggctat cctaatctat 780
atctgggtag catatgctat cctaatctat atctgggtag tatatgctat cctaatctgt 840
atccgggtag catatgctat cctcat 866

<210> SEQ ID NO 11
<211> LENGTH: 308
<212> TYPE: PRT
<213> ORGANISM: Artificial
<220> FEATURE:
<223> OTHER INFORMATION: Protein coded by EBNA1c-CO

<400> SEQUENCE: 11

```
Met Arg Gly Arg Gly Gly Ser Gly Gly Arg Gly Arg Gly Gly Ser Gly
1               5                   10                  15

Gly Arg Arg Gly Arg Gly Arg Glu Arg Ala Arg Gly Gly Ser Arg Glu
            20                  25                  30

Arg Ala Arg Gly Arg Gly Arg Gly Arg Gly Glu Lys Arg Pro Arg Ser
        35                  40                  45

Pro Ser Ser Gly Ala Gln Ser Ser Ser Ser Gly Ser Pro Pro Arg Arg
    50                  55                  60

Pro Pro Pro Gly Arg Arg Pro Phe Phe His Pro Val Gly Glu Ala Asp
65                  70                  75                  80

Tyr Phe Glu Tyr His Gln Glu Gly Gly Pro Asp Gly Glu Pro Asp Val
                85                  90                  95

Pro Pro Gly Ala Ile Glu Gln Gly Pro Ala Asp Asp Pro Gly Glu Gly
            100                 105                 110

Pro Ser Thr Gly Pro Arg Gly Gln Gly Asp Gly Ala Arg Arg Lys Lys
```

```
        115                 120                 125

Gly Gly Trp Phe Gly Lys His Arg Gly Gln Gly Gly Ser Asn Pro Lys
    130                 135                 140

Phe Glu Asn Ile Ala Glu Gly Leu Arg Ala Leu Leu Ala Arg Ser His
145                 150                 155                 160

Val Glu Arg Thr Thr Asp Glu Gly Thr Trp Val Ala Gly Val Phe Val
                165                 170                 175

Tyr Gly Gly Ser Lys Thr Ser Leu Tyr Asn Leu Arg Arg Gly Thr Ala
            180                 185                 190

Leu Ala Ile Pro Gln Cys Arg Leu Thr Pro Leu Ser Arg Leu Pro Phe
        195                 200                 205

Gly Met Ala Pro Gly Pro Gly Pro Gln Pro Gly Pro Leu Arg Glu Ser
    210                 215                 220

Ile Val Cys Tyr Phe Met Val Phe Leu Gln Thr His Ile Phe Ala Glu
225                 230                 235                 240

Val Leu Lys Asp Ala Ile Lys Asp Leu Val Met Thr Lys Pro Ala Pro
                245                 250                 255

Thr Cys Asn Ile Arg Val Thr Val Cys Ser Phe Asp Asp Gly Val Asp
            260                 265                 270

Leu Pro Pro Trp Phe Pro Pro Met Val Glu Gly Ala Ala Ala Glu Gly
        275                 280                 285

Asp Asp Gly Asp Asp Gly Asp Glu Gly Gly Asp Gly Asp Glu Gly Glu
    290                 295                 300

Glu Gly Gln Glu
305


<210> SEQ ID NO 12
<211> LENGTH: 337
<212> TYPE: PRT
<213> ORGANISM: Artificial
<220> FEATURE:
<223> OTHER INFORMATION: Protein coded by EBNA1s-CO

<400> SEQUENCE: 12

Met Arg Arg Gly Gly Asp Asn His Gly Arg Gly Arg Gly Arg Gly Arg
1               5                   10                  15

Gly Arg Gly Gly Gly Arg Pro Gly Ala Pro Gly Gly Ser Gly Ser Gly
            20                  25                  30

Pro Arg His Arg Asp Gly Val Arg Arg Pro Gln Lys Arg Pro Ser Cys
        35                  40                  45

Ile Gly Cys Lys Gly Thr His Gly Gly Thr Gly Ala Gly Ala Gly Ala
    50                  55                  60

Gly Gly Ala Gly Ala Gly Gly Gly Gly Glu Lys Arg Pro Arg Ser Pro
65                  70                  75                  80

Ser Ser Gln Ser Ser Ser Ser Gly Ser Pro Pro Arg Arg Pro Pro Pro
                85                  90                  95

Gly Arg Arg Pro Phe Phe His Pro Val Gly Glu Ala Asp Tyr Phe Glu
            100                 105                 110

Tyr His Gln Glu Gly Gly Pro Asp Gly Glu Pro Asp Val Pro Pro Gly
        115                 120                 125

Ala Ile Glu Gln Gly Pro Ala Asp Asp Pro Gly Glu Gly Pro Ser Thr
    130                 135                 140

Gly Pro Arg Gly Gln Gly Asp Gly Ala Arg Arg Lys Lys Gly Gly Trp
145                 150                 155                 160

Phe Gly Lys His Arg Gly Gln Gly Gly Ser Asn Pro Lys Phe Glu Asn
```

```
                165                 170                 175

Ile Ala Glu Gly Leu Arg Ala Leu Leu Ala Arg Ser His Val Glu Arg
            180                 185                 190

Thr Thr Asp Glu Gly Thr Trp Val Ala Gly Val Phe Val Tyr Gly Gly
        195                 200                 205

Ser Lys Thr Ser Leu Tyr Asn Leu Arg Arg Gly Thr Ala Leu Ala Ile
    210                 215                 220

Pro Gln Cys Arg Leu Thr Pro Leu Ser Arg Leu Pro Phe Gly Met Ala
225                 230                 235                 240

Pro Gly Pro Gly Pro Gln Pro Gly Pro Leu Arg Glu Ser Ile Val Cys
                245                 250                 255

Tyr Phe Met Val Phe Leu Gln Thr His Ile Phe Ala Glu Val Leu Lys
            260                 265                 270

Asp Ala Ile Lys Asp Leu Val Met Thr Lys Pro Ala Pro Thr Cys Asn
        275                 280                 285

Ile Arg Val Thr Val Cys Ser Phe Asp Asp Gly Val Asp Leu Pro Pro
    290                 295                 300

Trp Phe Pro Pro Met Val Glu Gly Ala Ala Ala Glu Gly Asp Asp Gly
305                 310                 315                 320

Asp Asp Gly Asp Glu Gly Gly Asp Gly Asp Glu Gly Glu Glu Gly Gln
                325                 330                 335

Glu
```

<210> SEQ ID NO 13
<211> LENGTH: 927
<212> TYPE: DNA
<213> ORGANISM: Artificial
<220> FEATURE:
<223> OTHER INFORMATION: EBNA1c-CO cDNA

<400> SEQUENCE: 13

```
atgcggggca gaggcggcag cggcggcaga ggaagaggcg gctctggcgg cagacgggga     60
agaggacgcg aaagagctag gggagggagc cgggagagag ccagaggcag aggccgggga    120
cggggcgaga agcggcccag aagccccagc tctggcgccc agtcctcttc tagtgggtcc    180
ccccccagaa ggccccctcc cggcaggcgg cccttcttcc accccgtggg cgaggccgac    240
tacttcgagt accatcagga aggcggacca gacggcgagc ccgacgtgcc tcctggggcc    300
atcgaacagg gccccgccga cgatcctggc gagggaccca gcaccggccc tcgaggacag    360
ggagacggcg ccaggcggaa gaagggcggc tggttcggca agcacagagg ccagggaggg    420
tccaacccca agttcgagaa tatcgccgag ggcctgagag ccctgctggc ccggtcccac    480
gtggagcgga ccaccgacga gggcacctgg gtggccggcg tgttcgtgta cggcggcagc    540
aagaccagcc tgtacaacct gcggagaggc accgccctgg ccatcccca gtgccggctg    600
acaccactct cccgcctccc ttttggcatg gctccagggc ctggacctca gcctggcccc    660
ctgcgggaga gcatcgtgtg ctacttcatg gtgtttctgc agacccacat cttcgccgag    720
gtgctgaagg acgccatcaa ggacctggtg atgaccaagc ctgcccccac ctgcaacatc    780
cgggtgaccg tgtgcagctt cgacgacggc gtggacctgc ccccctggtt ccccccccatg    840
gtggaaggag ccgctgcaga gggcgacgat ggcgatgatg gtgacgaagg tggggacggc    900
gacgaaggcg aggaaggcca ggaatga                                        927
```

<210> SEQ ID NO 14
<211> LENGTH: 1014

```
<212> TYPE: DNA
<213> ORGANISM: Artificial
<220> FEATURE:
<223> OTHER INFORMATION: EBNA1s-CO cDNA

<400> SEQUENCE: 14

atgcggagag gcggcgacaa ccacggcagg ggcagaggcc ggggaagagg cagaggcggc     60

ggaaggcctg gcgcccctgg cggcagcggc tccggcccca gacaccggga cggcgtgcgg    120

agaccccaga agcggcccag ctgcatcggc tgcaagggca cccacggcgg cacaggcgct    180

ggcgcagggg ctggcggagc cggagccggg ggagggggcg agaagaggcc cagaagcccc    240

agcagccaga gcagcagcag cggcagcccc cccagaaggc cccctcccgg caggcggccc    300

ttcttccacc ccgtgggcga ggccgactac ttcgagtacc accaggaagg cggccctgac    360

ggcgagcccg acgtgcctcc tggcgccatc gagcagggcc ccgccgacga tcctggcgag    420

ggacccagca ccggccctcg aggacaggga gacggcgcca ggcggaagaa gggcggctgg    480

ttcggcaagc acagaggcca gggagggtcc aaccccaagt tcgagaatat cgccgagggc    540

ctgagagccc tgctggcccg gtcccacgtg gagcggacca ccgacgaggg cacctgggtg    600

gccggcgtgt tcgtgtacgg cggcagcaag accagcctgt acaacctgcg gagaggcacc    660

gccctggcca tcccccagtg ccggctgaca ccactctccc gcctcccttt tggcatggct    720

ccagggcctg gacctcagcc tggcccccctg cgggagagca tcgtgtgcta cttcatggtg    780

tttctgcaga cccacatctt cgccgaggtg ctgaaggacg ccatcaagga cctggtgatg    840

accaagcctg cccccacctg caacatccgg gtgaccgtgt gcagcttcga cgacggcgtg    900

gacctgcccc cctggttccc ccccatggtg gaaggagccg ctgcagaggg cgacgatggc    960

gatgatggtg acgaaggtgg ggacggcgac gaaggcgagg aaggccagga atga         1014


<210> SEQ ID NO 15
<211> LENGTH: 78
<212> TYPE: PRT
<213> ORGANISM: Herpes Simplex Virus

<400> SEQUENCE: 15

Ala Pro Pro Thr Asp Val Ser Leu Gly Asp Glu Leu His Leu Asp Gly
1               5                   10                  15

Glu Asp Val Ala Met Ala His Ala Asp Ala Leu Asp Asp Phe Asp Leu
            20                  25                  30

Asp Met Leu Gly Asp Gly Asp Ser Pro Gly Pro Gly Phe Thr Pro His
        35                  40                  45

Asp Ser Ala Pro Tyr Gly Ala Leu Asp Met Ala Asp Phe Glu Phe Glu
    50                  55                  60

Gln Met Phe Thr Asp Ala Leu Gly Ile Asp Glu Tyr Gly Gly
65                  70                  75
```

PROCESS, VECTORS AND ENGINEERED CELL LINES FOR ENHANCED LARGE-SCALE TRANSFECTION

CROSS-REFERENCE TO RELATED APPLICATIONS

This application is a division of U.S. patent application Ser. No. 12/989,898 filed Oct. 27, 2010, currently pending, which is a continuation-in-part of U.S. patent application Ser. No. 11/576,005 filed Mar. 26, 2007, currently pending, and a national stage filing under 35 U.S.C. §371 of international application PCT/CA2009/000263 filed Mar. 9, 2009, which claims the benefit under 35 U.S.C. 119(e) of U.S. provisional patent application Ser. No. 61/071,760 filed May 15, 2008, the entire contents of all of which are herein incorporated by reference.

FIELD OF THE INVENTION

The present invention relates to processes, vectors and engineered cell lines for large-scale transfection and protein production.

BACKGROUND OF THE INVENTION

Large-scale transfection of Chinese Hamster Ovary (CHO) cells with cost-effective reagents for the production of r-proteins suffers from low efficiency and low productivity. In addition, plasmid vectors used in CHO cells are not fully optimized for transient gene expression.

There are some very efficient and commercially available cationic lipids formulation that can be used to transfect CHO cells in serum-free medium, for example FreestyleMax™ from Invitrogen. However, these cationic lipids are very expensive. Also, to improve productivity, it is becoming current practice to lower the cultivation temperature following transfection to prolong the production phase and to enhance productivity. This temperature shift is not “user friendly” when working at large-scale or when using non-refrigerated culture devices (Wave bioreactors, etc). Also, the exact temperature at which the shifts are done may be critical for getting optimal enhancement (e.g. 29 vs. 30 vs. 31 vs. 32 degrees Celsius).

International patent publication WO 2007/048601 reports an expression system in CHO cells stably expressing EBNA1 for the production of r-proteins. However, this document specifically admonishes that the cell lines shall not contain a functional copy of the Epstein-Barr virus (EBV) oriP sequence. Further, the full length EBNA1 structural gene encoding a full length EBNA1 protein is transfected into the cell line, and the oriP sequence is never in the same vector as the EBNA1 gene construct.

International patent publication WO 2002/090533 describes enhanced production of recombinant proteins by transient transfection of suspension-growing mammalian cells. However, only full length EBNA1 structural genes are used encoding full length EBNA1 proteins and only transient expression of a gene of interest is achieved.

International patent publication 2006/096989 describes expression vectors for enhanced transient gene expression and mammalian cells expressing them. However, only HEK293 cell lines are exemplified and the expression system used does not contain both the EBNA1 gene construct and the oriP sequence in the same vector. Further, only transient expression of a gene of interest is achieved.

There is a need in the art for processes, vectors and engineered cell lines for more efficient and productive transfection of cells at a large scale.

SUMMARY OF THE INVENTION

In accordance with a first aspect of the present invention, there is provided an expression system for stable expression of a gene of interest, the expression system comprising one vector having an Epstein-Barr virus nuclear antigen-1 (EBNA1) nucleotide sequence encoding a truncated EBNA1 protein, a promoter and a polyadenylation signal for the EBNA1 nucleotide sequence, an oriP nucleotide sequence, the gene of interest and a promoter and a polyadenylation signal for the gene of interest.

In accordance with a second aspect of the present invention, there is provided a method of stably expressing a gene of interest in mammalian cells, the method comprising: transfecting a mammalian cell with a vector having an Epstein-Barr virus nuclear antigen-1 (EBNA1) nucleotide sequence encoding a truncated EBNA1 protein, a promoter and a polyadenylation signal for the EBNA1 nucleotide sequence, an oriP nucleotide sequence, the gene of interest and a promoter and a polyadenylation signal for the gene of interest; and, replicating the cell to provide mammalian cells that stably express the gene of interest.

In accordance with a third aspect of the present invention, there is provided an expression system for stable expression of a gene of interest, the expression system comprising: a first vector having an Epstein-Barr virus nuclear antigen-1 (EBNA1) nucleotide sequence encoding a truncated EBNA1 protein, a promoter and a polyadenylation signal for the EBNA1 nucleotide sequence and an oriP nucleotide sequence; and, a second vector having a gene of interest, a promoter and a polyadenylation signal for the gene of interest and an oriP nucleotide sequence.

In accordance with a fourth aspect of the present invention, there is provided a method of stably expressing a gene of interest in mammalian cells, the method comprising transfecting a mammalian cell with: a first vector having an Epstein-Barr virus nuclear antigen-1 (EBNA1) nucleotide sequence encoding a truncated EBNA1 protein, a promoter and a polyadenylation signal for the EBNA1 nucleotide sequence and an oriP nucleotide sequence; and, a second vector having the gene of interest, a promoter and a polyadenylation signal for the gene of interest and an oriP nucleotide sequence to provide mammalian cells that stably express the gene of interest.

In the fourth aspect, transfecting the cell with the first and second vectors may be accomplished simultaneously, or the cell may be transfected by one of the vectors first to produce a stable clone followed by transfection with the other vector to produce a clone that stably expresses the gene of interest.

In accordance with a fifth aspect of the present invention, there is provided a method of transiently expressing a gene of interest in Chinese Hamster Ovary (CHO) cells, the method comprising: transfecting a CHO cell with a first vector having an Epstein-Barr virus nuclear antigen-1 (EBNA1) nucleotide sequence encoding a truncated EBNA1 protein, a promoter and a polyadenylation signal for the EBNA1 nucleotide sequence and an oriP nucleotide sequence, and a second vector having the gene of interest and a promoter and a polyadenylation signal for the gene of interest; and, replicating the cell to provide CHO cells that transiently express the gene of interest.

In the fifth aspect, transfecting the CHO cell with the first and second vectors may be accomplished simultaneously, or the CHO cell may be transfected by one of the vectors first to produce a clone followed by transfection with the other vector to produce a clone that transiently expresses the gene of interest.

In accordance with a sixth aspect of the present invention, there is provided a use of a codon-optimized Epstein-Barr virus nuclear antigen-1 (EBNA1) nucleotide sequence in an expression system for expressing a gene of interest in mammalian cells.

In accordance with a seventh aspect of the present invention, there is provided a fusion protein comprising: a truncated Epstein-Barr virus nuclear antigen-1c (EBNA1c) protein; and, a herpes simplex virus protein VP16.

In accordance with an eighth aspect of the present invention, there is provided a use of a 40 kDa fully deacetylated poly(ethylenimine) as a transfection reagent for improving transfection efficiency in transfection of Chinese Hamster Ovary (CHO) cells.

In accordance with a ninth aspect of the present invention, there is provided a use of co-expression of a fibroblast growth factor (FGF) to increase heterologous gene expression in Chinese Hamster Ovary (CHO) cells.

In accordance with a tenth aspect of the present invention, there is provided a use of protein kinase B to potentiate valproic acid (VPA) to increase heterologous gene expression in mammalian cells.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Materials and Methods:

Cell culture: CHO cells are grown at 37° C. in FreestyleCHO medium (Invitrogen) supplemented with 8 mM glutamine in Erlenmeyer flasks shaken at 120 rpm in a humidified atmosphere containing 5% $CO_2$. Cells are routinely maintained between $0.1\times10^6$ and $3.0\times10^6$ cells/ml. HEK293-EBNA1 cells (clone 6E) are grown at 37° C. in F17 medium (Invitrogen) supplemented with 4 mM glutamine and 0.1% pluronic F68 in Erlenmeyer flasks shaken at 120 rpm in a humidified atmosphere containing 5% $CO_2$. Cells are routinely maintained between $0.1\times10^6$ and $2.0\times10^6$ cells/ml.

Cell transfection: For transfection, CHO or HEK293 cells are grown in maintenance medium until they reach a density of $1.5\times10^6$ to $2.0\times10^6$ cells/ml and then the transfection mixture is added to the cells. For every ml of HEK293 cells to be transfected, 1 μg of plasmid DNA is mixed with 2 μg of 25 kDa linear polyethylenimine as previously described (Durocher, Perret & Kamen, 2002) For every ml of CHO cells to be transfected, 1 μg of plasmid DNA is mixed with 8 μg of 25 kDa linear polyethylenimine or with 6 μg of 40 kDa linear and deacetylated PEI (PEIMAX™ from Polysciences. Inc, catalog #24765-2).

Secreted alkaline phosphatase activity determination: SEAP activity is measured as previously described using the colorimetric substrate paranitrophenyl phosphate (Durocher et al, 2000).

Single Vector EBV oriP-EBNA1 Stable Expression System:

Mammalian cells transfected with an expression system in which a single vector contains an Epstein-Barr virus nuclear antigen-1 (EBNA1) nucleotide sequence encoding a truncated EBNA1 protein, an Epstein-Barr Virus (EBV) oriP nucleotide sequence and a gene of interest unexpectedly provide enhanced stable expression of the gene of interest.

Figure 1:
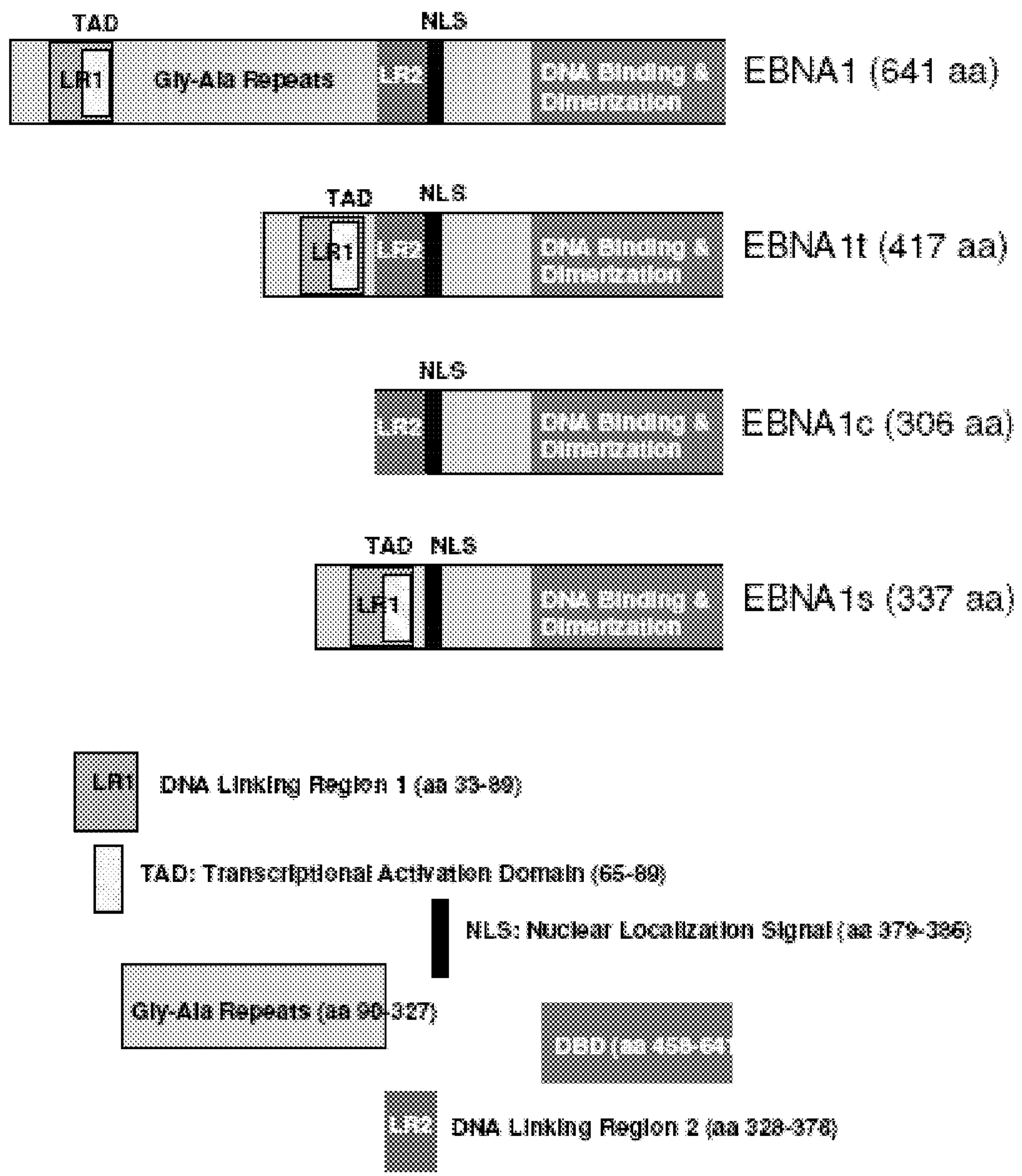
FIG. 1 depicts schematic diagrams of EBNA1 constructs.

Truncated EBNA1 proteins include, for example, EBNA1c, EBNA1t and EBNA1s. These truncated forms are shown in FIG. 1. EBNA1t is a 417 amino acid protein having DNA Linking Region 1 (LR1) containing Transcriptional Activation Domain (TAD) and DNA Linking Region 2 (LR2) without the Gly-Ala repeats of the 641 amino acid full length protein. EBNA1c is a 306 amino acid protein in which LR2 is present but LR1 is absent, and EBNA1s is a 337 amino acid protein in which LR1 is present but LR2 is absent. EBNA1 nucleotide sequences encoding EBNA1c are preferred in the vector. The amino acid sequences for the full length EBNA1 protein as well as the truncated forms EBNA1t, EBNA1c and EBNA1s are shown in SEQ ID NO: 1-4, respectively. The corresponding nucleotide sequences of the nucleic acid molecules encoding full length EBNA1 and the truncated forms are shown in SEQ ID NO: 5-8, respectively.

All or any functional part of the complete nucleotide sequence may be used in the vector. The EBV oriP complete nucleotide sequence (pTT3 vector) is shown in SEQ ID NO: 9, and a functional EBV oriP truncated nucleotide sequence (pTT5 vector) is shown in SEQ ID NO: 10. The oriP sequence comprises the Family of Repeats (FR) component and the dyad symmetry (DS) component. The oriP sequence, particularly the FR component, contributes to increased expression and stability of expression of the integrated truncated EBNA1 gene.

The gene of interest may be any gene that encodes a protein product of interest. Expression of the gene of interest in the transfected cells permits stable, large-scale production of the protein product for industrial purposes. Some particular genes of interest include, for example, genes that encode monoclonal antibodies, erythropoietins, interferons, vascular endothelial growth factors, stem cell growth factors, growth hormones, insulin-like growth factor binding proteins, etc.

The single vector also preferably comprises a selection gene to permit selection of the transfected cells for the propagation of stable cell lines. Any suitable selection gene may be used. One example of a class of such genes are genes that confer antibiotic resistance on the cell when the vector is transfected into the cell. Some examples within this class include genes that confer resistance to puromycin, blasticidin, geneticin, zeocin or hygromycin. The blasticidin resistance cassette as found in the pYD7 vector is particularly preferred. After transfection of a cell with the vector, the cell may be permitted to replicate. Clones possessing the expression system may be selected on the basis of the selection gene, for example, by treating the cells with an antibiotic and culturing the cells that survive. In this way, a cell line stably expressing the gene of interest may be created.

Any or all of the nucleotide sequences and/or genes in the integrated vector may be under the control of a promoter also incorporated in the vector. Generally, each gene has its own promoter. Thus, there is preferably a promoter for the EBNA1, a promoter for the gene of interest and a promoter for the selection gene. Strong or weak promoters may be used. Some promoters include, for example, the cytomegalovirus (CMV) promoter, Elongation Factor 1 alpha-HTLV (EF1α-HTLV) hybrid promoter, and Rous sarcoma virus (RSV) promoter. Also, any or all genes may have a polyadenylation signal. Alternatively, two genes, separated by an Internal Ribosome Entry Site (IRES), can be expressed by using only one promoter and one polyadenylation signal.

Figure 3A:
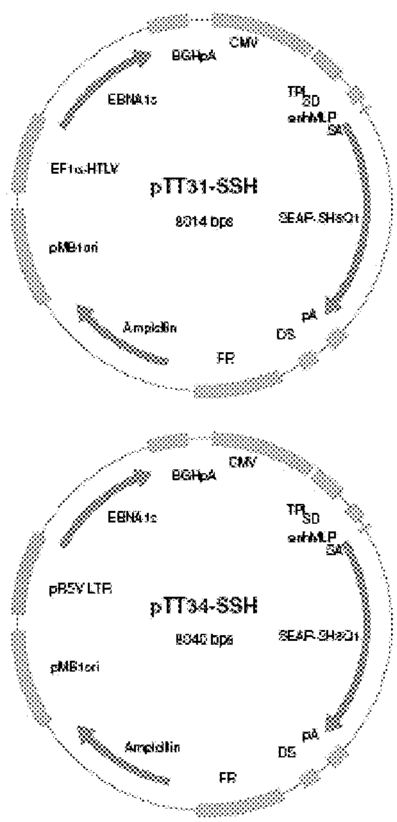
FIG. 3A depicts genetic maps of pTT vectors encoding EBNA1c in cis under a strong (EF1α-HTLV; pTT31) or a weak (RSV; pTT34) promoter.

Genetic maps of two embodiments (pTT31-SSH and pTT34-SSH) of the single vector are shown in FIG. 3A. pTT31-SSH is a 8014 bp vector in which the EBNA1c gene is under the control of a strong promoter (EF1α-HTLV) and the gene of interest (secreted alkaline phosphatase (SEAP) gene) is under the control of a strong promoter (CMV). pTT34-SSH is a 8040 bp vector in which the EBNA1c gene is under the control of a weaker promoter (RSV) and the gene of interest (secreted alkaline phosphatase (SEAP) gene) is under the control of a strong promoter (CMV).

Figure 3B:
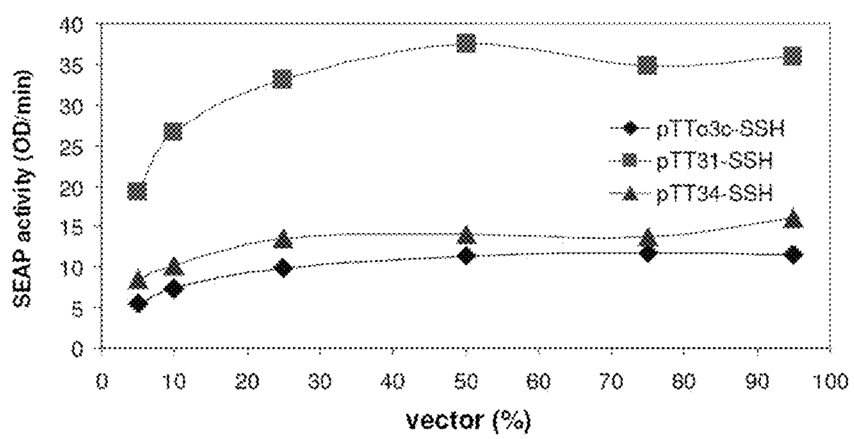
FIG. 3B depicts a graph of SEAP activity in CHO cells transfected with pTT vectors encoding EBNA1c in cis under a weak or strong promoter.

FIG. 3B depicts a graph of SEAP activity in CHO cells transfected with pTT vectors (oriP-containing vectors) encoding EBNA1c in cis under a weak (RSV) or strong (EF1α-HTLV) promoter. Referring to FIG. 3B, CHO cells were transfected with increasing amounts of the SEAP gene-containing plasmids pTT-SSH (with oriP but without EBNA1c), pTT31-SSH (with oriP and with EBNA1c under the control of the strong EF1α-HTLV promoter) and pTT34-SSH (with oriP and with EBNA1c under the control of the weak RSV promoter). Both EBNA1c-containing pTT vectors (pTT31-SSH and pTT34-SSH) lead to an increase in SEAP activity in CHO cells over the non-EBNA1c-containing vector (pTT-SSH). Use of a strong promoter to control EBNA1 expression optimizes levels of transactivating activity thereby optimizing expression of the gene of interest.

The single vector EBV oriP-EBNA1 expression system is useful in different types of mammalian cells, for example, Chinese Hamster Ovary (CHO) cells, human embryonic kidney 293 (HEK293) cells, Madin-Darby Canine Kidney (MDCK) cells, Vero cells and PER.C6™ cells, especially CHO cells.

Two Vector EBV oriP-EBNA1 Stable Expression System:

Mammalian cells transfected with an expression system comprising two separate vectors, a first vector containing an Epstein-Barr virus nuclear antigen-1 (EBNA1) nucleotide sequence encoding a truncated EBNA1 protein and an Epstein-Barr Virus (EBV) oriP nucleotide sequence, and a second vector comprising a gene of interest and an Epstein-Barr Virus (EBV) oriP nucleotide sequence unexpectedly provide enhanced stable expression of the gene of interest. The use of oriP in both vectors contributes to stability of expression and increased expression of the gene of interest. To facilitate production of stable cell lines that stably express the gene of interest, both vectors contain selection genes. Selection genes are described above. For example, a stable CHO cell clone expressing EBNA1c driven from an integrated oriP vector containing a blasticidin resistance cassette (pYD7) stably expressed the gene of interest for over 6 months in the absence of selection.

Stable mammalian cell lines can be produced either by simultaneously transfecting a cell with both vectors and then propagating the cell, or by transfecting a cell with one of the vectors (either the EBNA1-containing or the gene of interest-containing vector) to produce a stable clone and then transfecting a stable clone cell with the other of the vectors to produce a stable clone stably expressing the gene of interest.

Truncated EBNA1 proteins and corresponding genes, as well as the oriP and genes of interest are described above. As described previously, genes may be under the control of promoters. The two vector EBV oriP-EBNA1 stable expression system is also useful in different types of mammalian cells, for example, Chinese Hamster Ovary (CHO) cells, human embryonic kidney 293 (HEK293) cells, Madin-Darby Canine Kidney (MDCK) cells and PER.*C6*™ cells, especially CHO cells.

Figure 11:
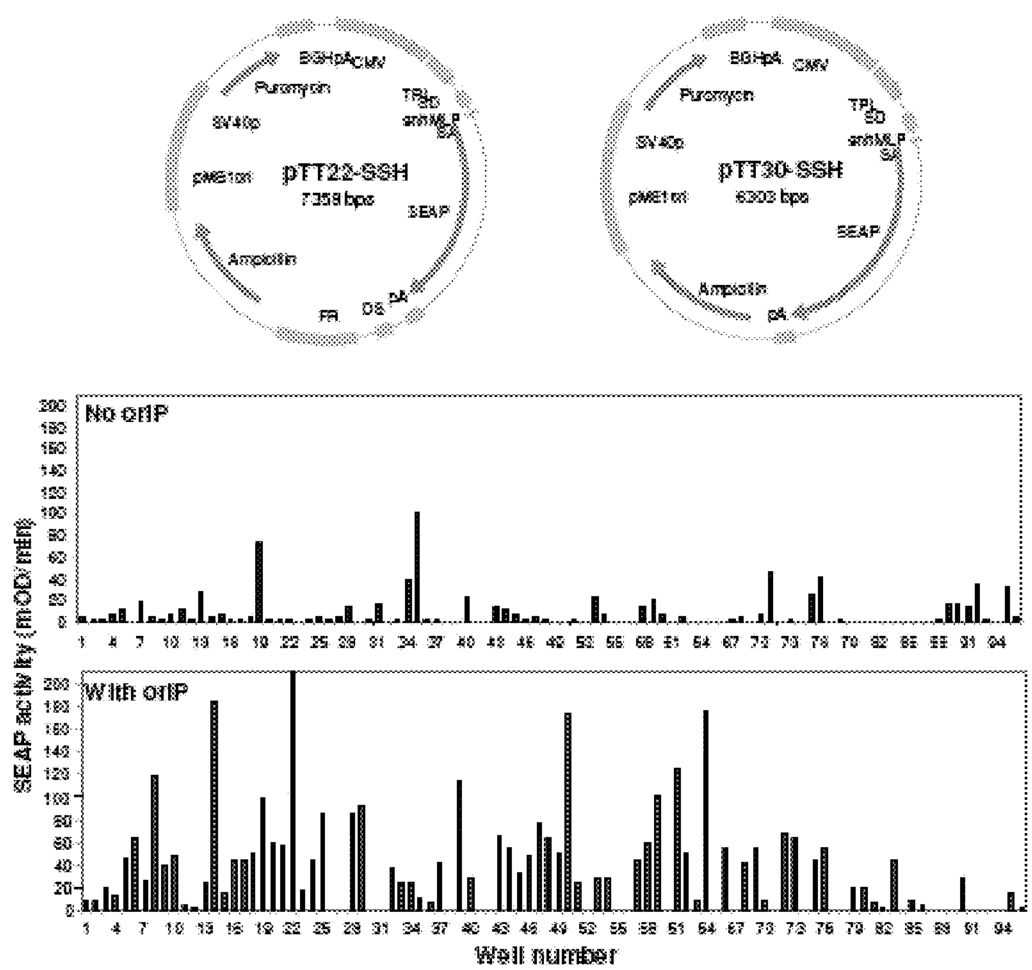
FIG. 11 depicts genetic maps of SEAP-encoding pTT plasmids pTT22 (+oriP) and pTT30 (oriP) and graphs of SEAP activity in CHO-EBNA1c cells transfected with linearized pTT22 and pTT30 plasmids illustrating the effect of oriP on linearized vectors in CHO-EBNA1c cells.
Figure 12:
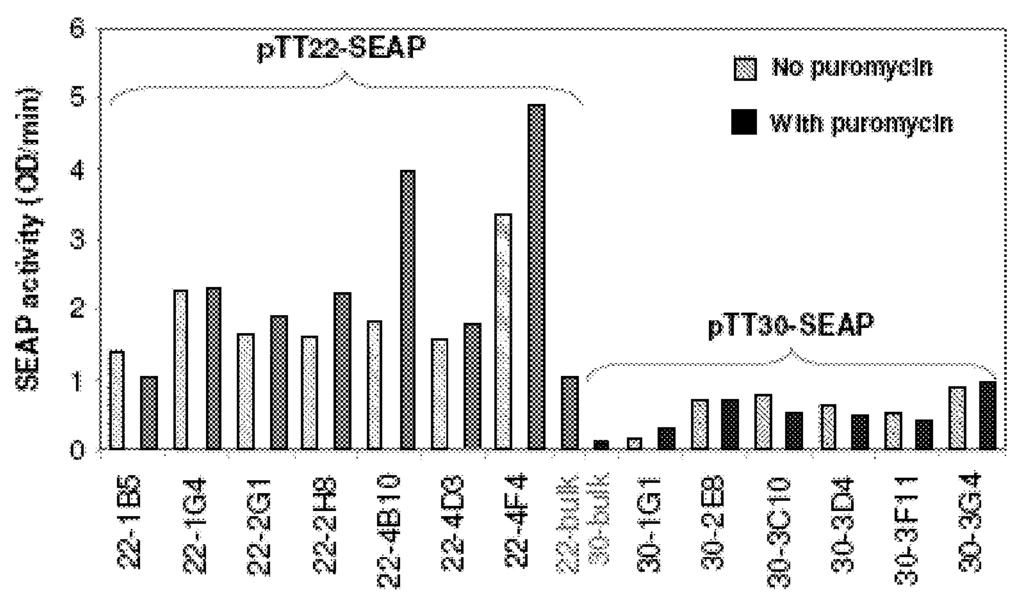
FIG. 12 depicts a graph of SEAP activity in CHO-EBNA1c cells after integration of linearized pTT22 (+oriP) and pTT30 (−oriP) plasmids in their chromosomes.

Referring to FIGS. 11 and 12, Chinese Hamster Ovary (CHO) cells stably expressing EBNA1c were produced by transfecting CHO cells with an EBNA1c oriP-containing plasmid (pYD7 vector) using generally known methods with a linear 25 kDa polyethylenimine (PEI), and stable clones were propagated. One CHO-EBNA1c clone (clone 3E7) so produced was transfected with secreted alkaline phosphatase (SEAP)-encoding and linearized pTT22 (+oriP) or pTT30 (−oriP) vectors. The pTT22 and pTT30 vectors both contain a puromycin resistance cassette. The pTT22 vector contains oriP (i.e. the DS and FR elements are present) while the pTT30 vector does not contain oriP (i.e. the DS and FR elements are removed). CHO-EBNA1c cells transfected with the pTT22 and pTT30 vectors were transferred in 96-well plates at a density of 100 cells/well. Puromycin was added 24 hours post-transfection and selection was maintained for two weeks.

Referring to FIG. 11, after selection, SEAP activity (mOD/min at 410 nm) was measured in the supernatant at day 14 post-transfection. The results clearly demonstrate the trans-activating action of EBNA1c on linearized oriP-bearing expression plasmids integrated in CHO cells. Linearization of the vector abolishes the replication potential of the oriP-EBNA1c system thus eliminating the possibility that the increased SEAP expression is due to plasmid replication. The average SEAP activity for the 96 wells are 46.5 and 5.8 mOD/min for oriP-containing and non-oriP-containing SEAP-encoding vectors, respectively.

Referring to FIG. 12, after selection, the best positive clones (7 clones for pTT22-oriP vector and 6 clones for pTT30-non-oriP vector) were amplified and maintained in 6-well plates with or without puromycin. Twenty days later, clones were seeded in a 6-well plate at 0.25 million cells per ml and SEAP activity (OD/min at 410 nm) was measured 5 days later. Also shown in FIG. 12 is the SEAP activity found in the non-cloned ("pools" or "bulk") transfected cells maintained in the presence of puromycin for 34 days. SEAP activity in the oriP bulk is 10 times higher than in the non-oriP bulk. These results clearly demonstrate the transactivating action of EBNA1c on integrated oriP-bearing expression plasmids in CHO cells. For clones 4B10 and 4F4, the increased SEAP activity in the presence of puromycin suggests that these two clones are non-clonal and probably contaminated by a cellular population expressing lower levels of SEAP. SEAP activity is expressed as increase in absorbance unit at 410 nm per min (OD/min).

Thus, the presence of oriP in the integrated expression plasmid confers higher expression levels of the gene of interest in EBNA1-expressing mammalian cells, particularly CHO cells, vs. non-oriP-containing plasmids.

Two Vector Transient Expression System in CHO Cells:

Chinese Hamster Ovary (CHO) cells transfected with an expression system comprising two separate vectors, a first vector containing an Epstein-Barr virus nuclear antigen-1 (EBNA1) nucleotide sequence encoding a truncated EBNA1 protein and an Epstein-Barr Virus (EBV) oriP nucleotide sequence, and a second vector comprising a gene of interest and an Epstein-Barr Virus (EBV) oriP nucleotide sequence also unexpectedly provide enhanced transient expression of the gene of interest in the CHO cells.

CHO cell lines can be produced either by simultaneously transfecting a cell with both vectors and then propagating the cell, or by transfecting a cell with one of the vectors (either the EBNA1-containing or the gene of interest-containing vector) to produce a clone and then transfecting a clone cell with the other of the vectors to produce a clone transiently expressing the gene of interest. Truncated EBNA1 proteins and corresponding genes, as well as the oriP and genes of interest are described above. As described previously, genes may be under the control of promoters.

Figure 2:
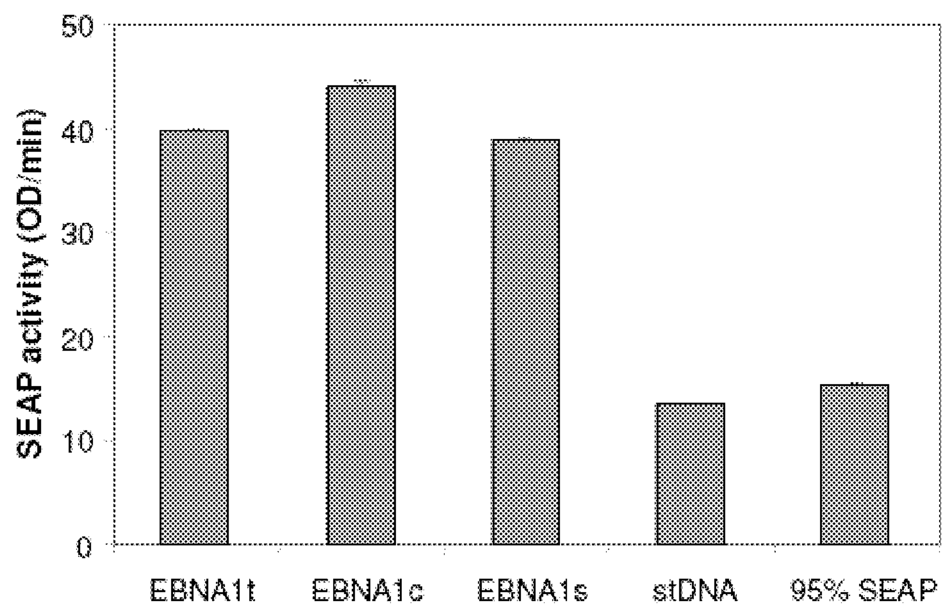
FIG. 2 depicts graphs of SEAP activity in CHO cells co-transfected with pTT vectors encoding various EBNA1 constructs.

FIG. 2 illustrates transient expression of secreted alkaline phosphatase (SEAP) in CHO cells co-transfected with one vector containing oriP plus the SEAP gene and another vector containing oriP plus truncated EBNA1 constructs (EBNA1t, EBNA1c and EBNA1s). In FIG. 2, CHO cells were co-transfected with 50% of pTT-EBNA1 constructs or 50% salmon testis DNA (stDNA) and (45% pTT-SEAP+5% pTT-GFP) plasmids. SEAP activity was compared to activity in CHO cells transfected with 95% pTT-SEAP+5% pTT-GFP. SEAP activity (OD/min at 410 nm) was measured 5 days post-transfection. Transfection was accomplished using generally known methods with a linear 25 kDa polyethylenimine (PEI).

The results in FIG. 2 show an increase in transient SEAP activity of 2-fold or higher in CHO cells co-transfected with oriP/EBNA1 and oriP/SEAP plasmids over CHO cells that are not co-transfected with oriP/EBNA1 plasmids. Further, while it has been previously shown that the "Transcriptional Activation Domain" (aa 65-89) in the LR1 domain of EBNA1 is essential for transcriptional activation of integrated oriP vectors, FIG. 2 surprisingly shows that the truncated EBNA1c construct lacking the LR1 domain but containing the LR2 domain is capable of increasing gene expression from non-integrated oriP plasmids to the same level as EBNA1t (that contains both the LR1 and LR2 domains) or EBNA1s (that contains only the LR1 domain).

Figure 4:
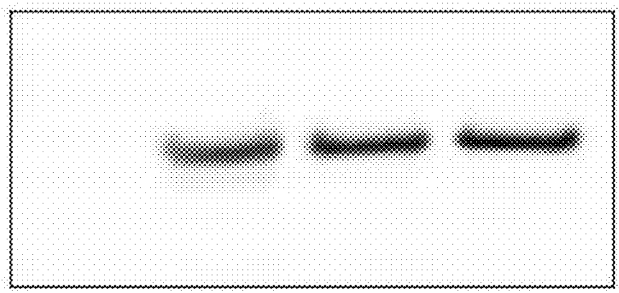
FIG. 4A depicts a Western blot of extracts from CHO cells transfected with a linearized pTT-EBNA1c vector containing a blasticidin resistance cassette.
FIG. 4B depicts a Western blot of aliquots of cultures of the CHO cells of FIG. 4A at various time intervals without selection pressure.
Figure 4:
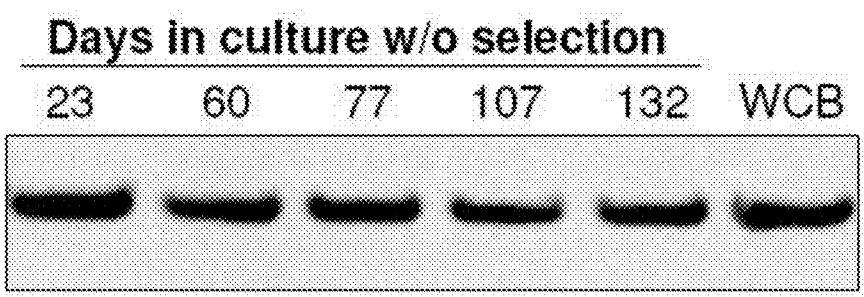

In FIG. 4, CHO cells were transfected with a linearized pTT-EBNA1c vector containing a blasticidin resistance cassette (pYD7 vector). Linearization of the vector was achieved following restriction enzyme digestion using PvuI enzyme. Following transfection, cells having stably integrated the pYD7 vector were selected by adding blasticidin to the culture medium. After a few days of blasticidin selection, blasticidin-resistant cells were seeded in 96-well plates without blasticidin selection. Emerging clones were tested for EBNA1c expression. An EBNA1c-positive clone, 3E7 (FIG. 4A), was then selected for further testing. A master cell bank (MCB) and Working cell bank (WCB) were made at this point. The CHO-EBNA1c (clone 3E7) cells were cultured for over 130 days in the absence of blasticidin selection. At various culture time points, an aliquot of the cells were taken for EBNA1c expression analysis by Western blot using an anti-EBNA1 antibody. FIG. 4B shows that the clone 3E7 is very stable over 130 days in culture without blasticidin selection pressure.

Figure 7:
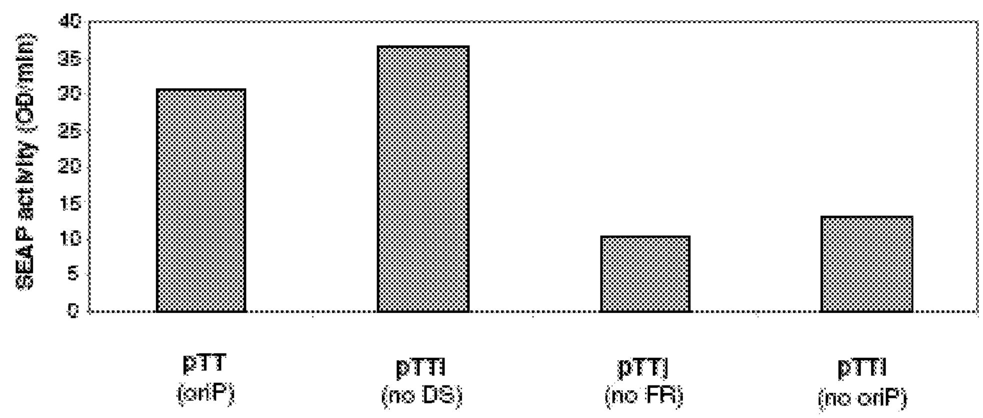
FIG. 7 depicts a graph of SEAP activity in transiently transfected CHO-EBNA1c cells illustrating the transactivating activity of oriP.

In FIG. 7, CHO cells containing integrated EBNA1-expressing plasmids were produced by transfecting CHO cells with a pTT-EBNA1c vector, and the clone propagated (clone 3E7). Resulting CHO-EBNA1c clone was transfected with SEAP-encoding pTT plasmids with complete oriP (pTT-SMH), with DS-deleted oriP (pTTi-SMH), with FR-deleted oriP (pTTj-SMH) or with oriP-deleted (pTTl-SMH) pTT vectors. SEAP activity (OD/min at 410 nm) was measured in the supernatant at 5 days post-transfection. Transfections were accomplished using generally known methods with a linear 25 kDa polyethylenimine (PEI).

The results in FIG. 7 illustrate that increased expression in transiently transfected CHO-EBNA1 cells is due to the transactivating activity of the oriP family of repeats (FR) element, and not to plasmid replication. Removal of the dyad symmetry (DS) element (EBNA1-dependent origin of replication) from the oriP does not inhibit expression while removing the FR element (responsible for EBNA1-dependent transcriptional activation) strongly reduces expression. The results also show that the DS element has a slight inhibitory effect on gene expression.

Figure 8:
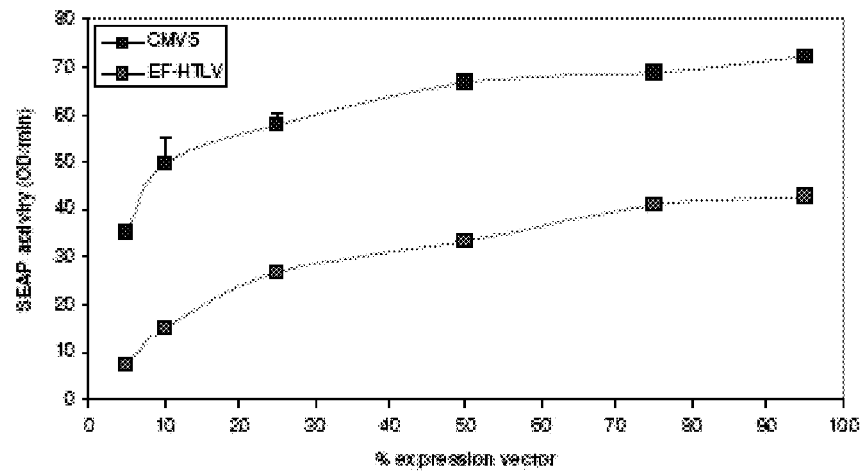
FIG. 8 depicts a graph of SEAP activity in transfected CHO-EBNA1c cells illustrating the effect of the CMV5 promoter vs. the Elongation Factor 1 alpha-HTLV (EF1α-HTLV) hybrid promoter.

FIG. 8 compares the effect of the cytomegalovirus (CMV5) promoter and elongation factor 1 alpha-HTLV (EF1-αHTLV) promoter on transgene expression in CHO-EBNA1c cells (clone 3E7). CHO-EBNA1c-3E7 cells were transfected with increasing amount SEAP-encoding oriP-containing (pTT) plasmids containing either the CMV5 or EF1-αHTLV promoter to control the SEAP gene (the overall content of DNA was kept constant by compensating with non-coding stDNA). SEAP activity (OD/min at 410 nm) was measured in the supernatant at day 6 post-transfection. The results clearly demonstrate that the CMV5 promoter is at least 5 times more potent than the EF1-αHTLV promoter at low plasmid doses (e.g. 5%). Further, CMV5-based plasmid needs 2-4 times less coding plasmid DNA for maximum expression.

Codon-Optimized EBNA1 Constructs:

Codon-optimization of Epstein-Barr virus nuclear antigen-1 (EBNA1) nucleotide sequence strongly enhances expression of EBNA1 in mammalian cells, especially Chinese Hamster Ovary (CHO) and human embryonic kidney (HEK) cells. A codon-optimized EBNA1 cDNA instead of non-codon-optimized EBNA1 cDNA may be used in any of the aspects of the present invention. Full length or truncated EBNA1 cDNA may be codon-optimized. Advantageously, such codon-optimized EBNA1 nucleotide sequences permit the use of weaker promoters to express EBNA1, thereby reducing the likelihood of promoter competition between two strong promoters in a single expression system. Codon-optimized EBNA1c nucleotide sequence (EBNA1c-CO, SEQ ID NO: 13) codes for a 308 amino acid protein (SEQ ID NO: 11). Codon-optimized EBNA1s nucleotide sequence (EBNA1s-CO, SEQ ID NO: 14) codes for a 337 amino acid protein (SEQ ID NO: 12).

Figure 5:
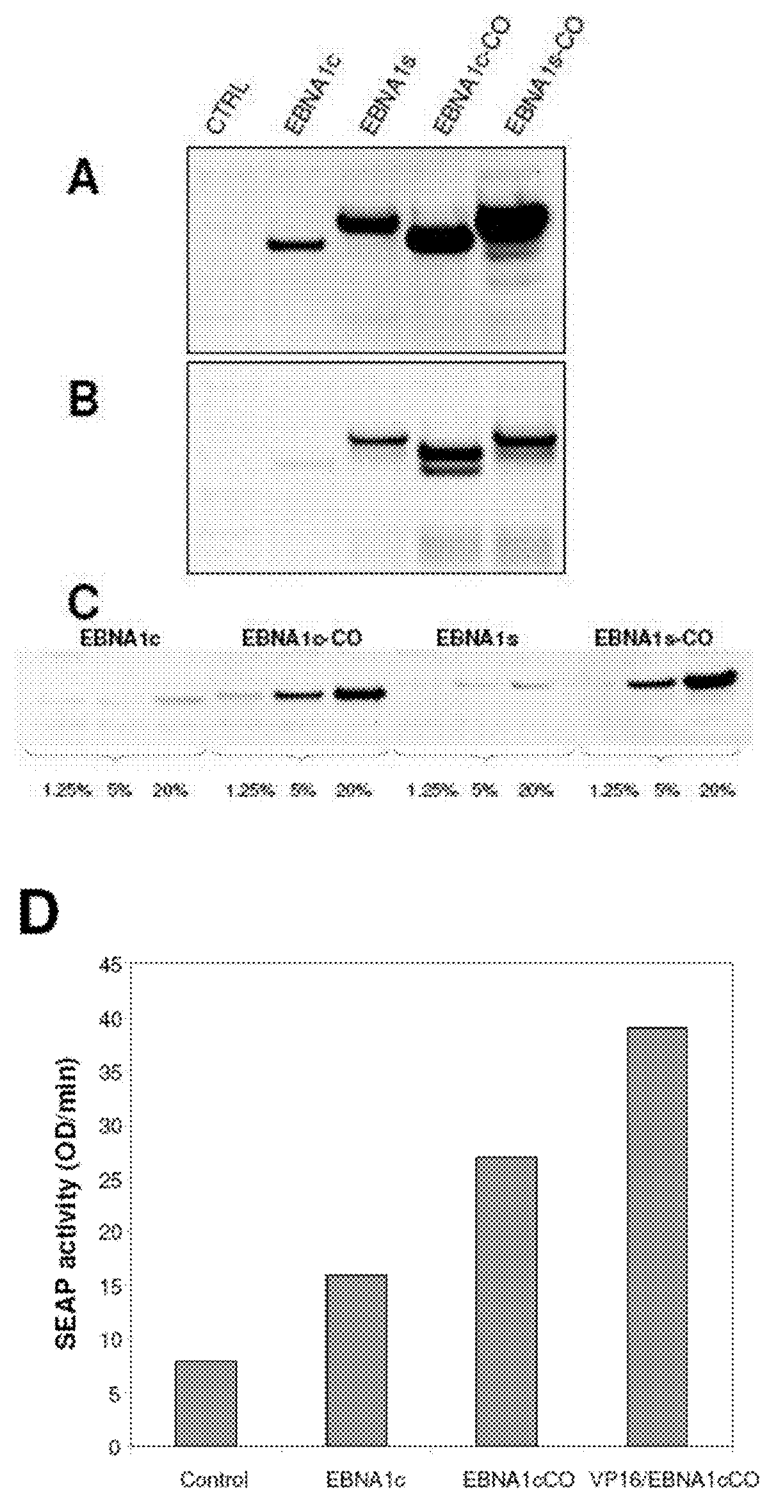
FIGS. 5A-C depict Western blots of codon optimized EBNA1 expression in HEK293 and CHO cells.
FIG. 5D depicts a graph of secreted alkaline phosphatase (SEAP) activity in CHO cells co-expressing VP16-EBNA1c fusion protein compared to control cells or cells expression an EBNA1c protein.

Referring to FIG. 5, EBNA1 constructs (EBNA1c and EBNA1s) were codon-optimized (human codon usage—CO). pTT vectors containing EBNA1c, EBNA1s or their codon-optimized versions (EBNA1c-CO (SEQ ID NO: 13) and EBNA1s-CO (SEQ ID NO: 14)), and empty pTT vector (CTRL) were transfected in separate HEK293 cells or CHO cells by generally known methods with a linear 25 kDa polyethylenimine (PEI). Three days post-transfection, cells were lyzed and cell extracts analyzed by Western blot using an anti-EBNA1 antibody. FIG. 5A is a Western blot for cell extracts from HEK293 cells and FIG. 5B is a Western blot for cell extracts from CHO cells. In both cell lines it is evident that codon optimization enhances transient expression of EBNA1 in the cells when compared to the control (CTRL) and the cells transfected with non-codon-optimized EBNA1.

For FIG. 5C, HEK293 cells were transfected with increasing amounts (1.25%, 5% and 20%) of pTT vectors containing EBNA1c, EBNA1c-CO, EBNA1s or EBNA1s-CO. Again it is evident from the Western blots in FIG. 5C that codon optimization enhances transient expression of EBNA1 in cells when compared to cells transfected with non-codon-optimized EBNA1.

For FIG. 5D, CHO cells were co-transfected with pTT-SEAP (50%) plus 5% pTT-GFP vectors (Control) with or without 10% of pTT-EBNA1c, pTT-EBNA1cCO or pTT-VP16/EBNA1cCO (EBNA1cCO fused at its N-terminus to VP16—see below). Non-coding DNA (stDNA) was used as stuffer DNA to complete the amounts of DNA to 100%. SEAP activity measured 5 days later. This clearly demonstrates that, by improving its expression, codon optimization of EBNA1c provides an increased transactivating activity. A VP16-EBNA1cCO chimera also further increases transient gene expression in CHO cells compared to EBNA1c and EBNA1cCO (see below).

EBNA1c-VP16 Fusion Protein:

A fusion protein comprising a truncated Epstein-Barr virus nuclear antigen-1c (EBNA1c) protein and a herpes simplex virus protein VP16 provides significantly enhanced transactivating activity in mammalian cells, particularly Chinese Hamster Ovary (CHO) cells and human embryonic kidney (HEK) cells.

A fusion protein is constructed by fusing VP16 to the N-terminus of codon-optimized EBNA1c. The VP16 cDNA encoding for the following protein sequence was used: APPTDVSLGDELHLDGEDVAMAHADALDDFDLDMLGDGDSPGPGFTPHDSAPY GALDMADFEFEQMFTDALGIDEYGG (SEQ ID NO: 15). The VP16 cDNA sequence was cloned in-frame to the 5' region of codon-optimized EBNA1c using generally known methods.

The VP16-EBNA1cCO fusion protein in a pTT plasmid (10%) was co-transfected in CHO cells with pTT-SEAP plasmid (50%) and pTT-GFP plasmid (5%) with a linear 40 kDa deacetylated polyethylenimine (see below). The CHO cells were transfected with 10% pTT/VP16-EBNA1cCO, 50% SEAP, 35% stDNA and 5% GFP. Non-coding DNA (stDNA) was used as stuffer DNA to complete the amounts of DNA to 100%. Five days post-transfection, SEAP activity (OD/min) was measured and compared to activities in cells transfected with stuffer DNA in place of pTT/EBNA1 vectors (CTRL), or a pTT/EBNA1c vector or a pTT/EBNA1cCO vector in place of pTT/VP16-EBNA1c (FIG. 5D). The results in FIG. 5D clearly demonstrate that a VP16-EBNA1cCO chimera further increases transient gene expression in CHO cells compared to EBNA1c or EBNA1cCO.

Transfection with Fully Deacylated PEI:

Use of a 40 kDa fully deacetylated poly(ethylenimine) (LPEI-MAX) as a transfection reagent unexpectedly improves transfection efficiency and/or productivity in Chinese Hamster Ovary (CHO) cells in comparison to the use of the usual linear 25 kDa poly(ethylenimine) (LPEI). Such an improvement is not realized in human embryonic kidney (HEK) cells.

Figure 6:
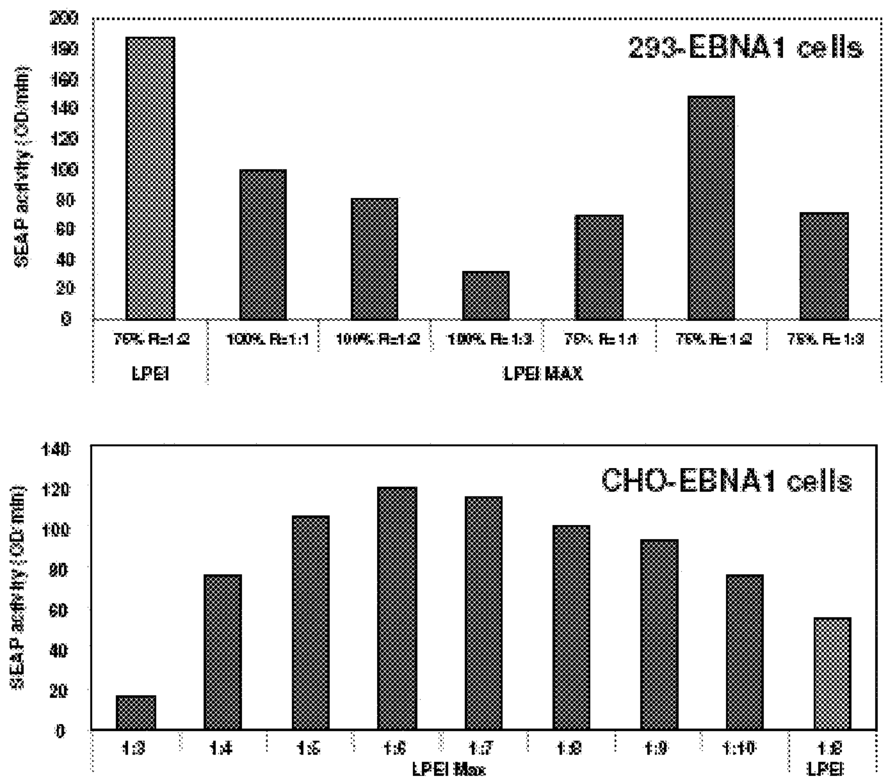
FIG. 6 depicts graphs of SEAP activity in HEK293 and CHO cells transfected with pTT plasmids using LPEI or LPEI-Max.

Referring to FIG. 6, HEK293-EBNA1t (clone 6E) and CHO-EBNA1c (clone 3E7) cells were used. For the upper panel of FIG. 6, HEK293-EBNA1t cells were transfected with pTT-SEAP plasmids using LPEI-MAX at various DNA:*P*EI ratios (R) and polyplexes amounts (%). SEAP activity (OD/min at 410 nm) was measured in the supernatant 6 days post transfection and compared to the best condition found for LPEI (75% polyplexes; R=1:2). The results in the upper panel show that LPEI-Max is not better than LPEI in HEK293 cells. For the lower panel, CHO-EBNA1 cells were transfected with pTT-SEAP plasmids using LPEI-MAX at various DNA:*P*EI ratios. SEAP activity (OD/min at 410 nm) was measured in the supernatant 6 days post transfection and compared to the best condition found for LPEI (1:8). The results in the lower panel clearly demonstrate that LPEI-MAX is significantly more potent than LPEI in CHO cells for transient gene expression.

Co-Expression of FGF:

Co-expression of a fibroblast growth factor (FGF) increases heterologous gene expression in Chinese Hamster Ovary (CHO) cells.

Figure 9:
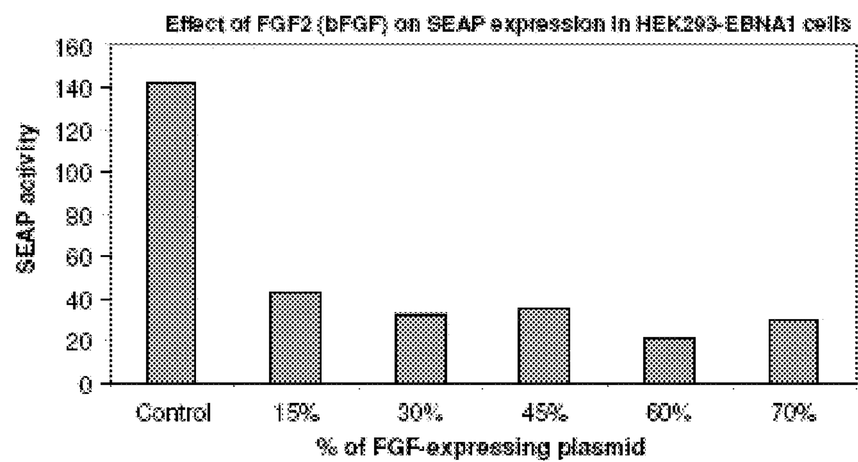
FIG. 9 depicts graphs of SEAP activity illustrating the effect of FGF2 (bFGF) co-expression on transient gene expression in HEK293-EBNA1t and CHO-EBNA1c cells.
Figure 9:
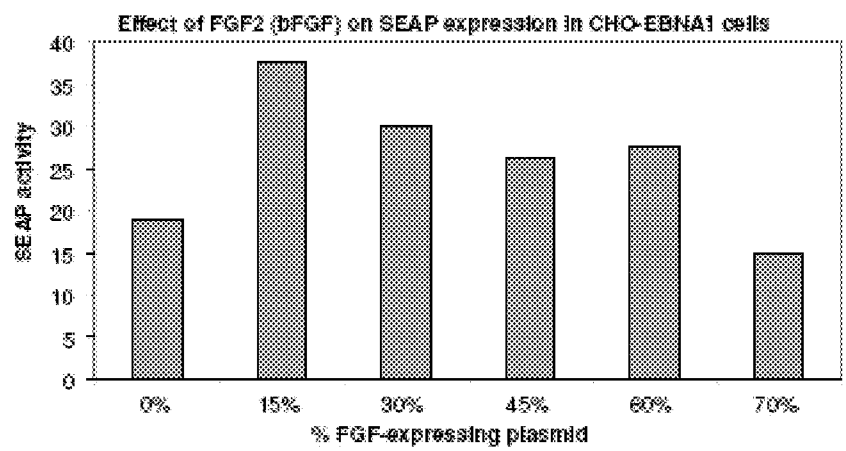

Referring to FIG. 9, graphs are shown illustrating the effect of FGF2 (bFGF) co-expression on transient gene expression in HEK293-EBNA1t (clone 6E) cells (upper panel) and CHO-EBNA1c (clone 3E7) cells (lower panel). The HEK293-EBNA1t and CHO-EBNA1c cells were transfected with 25% pTT-SEAP vector and increasing amounts (0%, 15%, 30%, 45%, 60% and 70%) of FGF2-encoding pTT plasmid (the overall content of DNA was kept constant with non-coding stDNA). SEAP activity (OD/min at 410 nm) was measured in the supernatant 7 days post-transfection. From the upper panel it is evident that SEAP activity in HEK293-EBNA1t cells is decreased by co-expression of FGF2. From the lower panel it is evident that SEAP activity in CHO-EBNA1c cells is increased by co-expression of FGF2. This clearly demonstrates that the co-expression of FGF2 enhances transgene expression in CHO cells but not in HEK293 cells. Increased productivity in CHO cells may be due to a FGF-induced rRNA synthesis.

PKB Potentiation of VPA:

Use of protein kinase B (PKB) to potentiate valproic acid (VPA) increases heterologous gene expression in mammalian cells, especially Chinese Hamster Ovary (CHO) cells.

Valproic acid (VPA), a histone deacetylase inhibitor, enhances transient gene expression in cells. However, VPA also induces apoptosis thereby killing cells and reducing overall gains in productivity. It has now been found that co-expressing PKB (also known as AKT) or a constitutively active PKB mutant in the cells potentiates the action of valproic acid in gene expression by inhibiting apoptosis.

Figure 10:
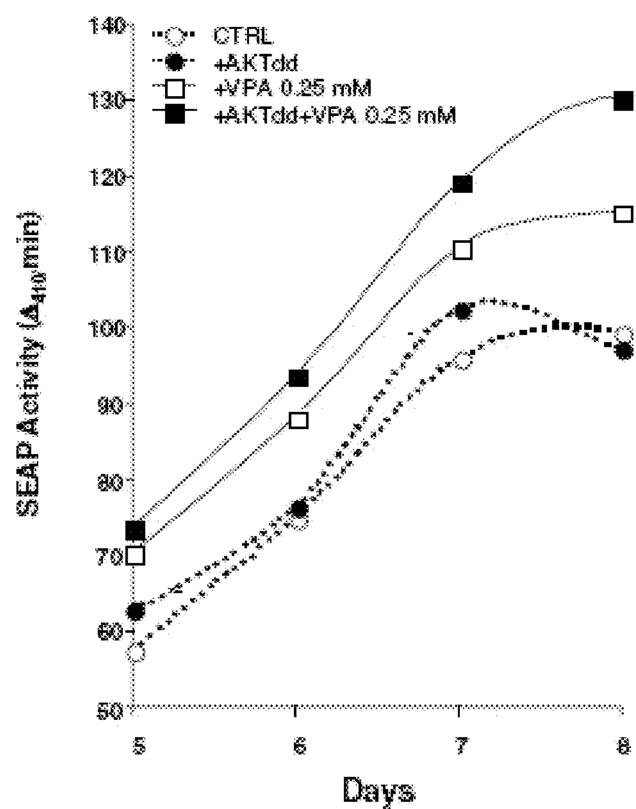
FIG. 10 depicts a graph of SEAP expression in CHO-EBNA1c cells illustrating protein kinase B (AKT) potentiation of valproic acid (VPA) enhancement of transient gene expression.

Referring to FIG. 10, the effect of PKB (AKT) and valproic acid (VPA) on transient gene expression in CHO-EBNA1c (clone 3E7) cells is illustrated. The CHO-EBNA1c cells were transfected with a mixture of SEAP-encoding oriP plasmids (pTT-SEAP) and stuffer DNA or pTT-AKTdd vector (AKTdd is a dominant-positive mutant of AKT). In some cases, 0.25 mM VPA was added 24 hours post-transfection. SEAP activity (ΔA410/min) was measured at days 5 to 8 post-transfection. FIG. 10 clearly demonstrates that valproic acid increases transient gene expression in CHO cells and that transient co-expression of AKTdd greatly potentiates this effect.

REFERENCES

The contents of the entirety of each of which are incorporated by this reference.

Mizuguchi H, Hosono T, Hayakawa T. Long-term replication of Epstein-Barr virus-derived episomal vectors in the rodent cells. *FEBS Lett* 2000 Apr. 28; 472(2-3):173-8.

Durocher, Y, Perret, S, Thibaudeau, E, Gaumond, M H, Kamen, A, Stocco, R, Abramovitz, M. A reporter gene assay for high-throughput screening of G-protein-coupled receptors stably or transiently expressed in HEK293 EBNA cells grown in suspension culture. *Analytical Biochemistry* 2000 Sep. 10, 284 (2):316-26.

Boussif O, Zanta M A, Behr J P. Optimized galenics improve in vitro gene transfer with cationic molecules up to 1000-fold. *Gene Ther* 1996 December; 3(12):1074-80.

Thomas M, Lu J J, Ge Q, Zhang C, Chen J, Klibanov A M. Full deacylation of polyethylenimine dramatically boosts its gene delivery efficiency and specificity to mouse lung. *Proc Natl Acad Sci USA* 2005 Apr. 19; 102(16):5679-84.

Kang M S, Hung S C, Kieff E. Epstein-Barr virus nuclear antigen 1 activates transcription from episomal but not integrated DNA and does not alter lymphocyte growth. *Proc Natl Acad Sci USA* 2001 Dec. 18; 98(26):15233-8.

Sears J, Kolman J, Wahl G M, Aiyar A. Metaphase chromosome tethering is necessary for the DNA synthesis and maintenance of oriP plasmids but is insufficient for transcription activation by Epstein-Barr nuclear antigen 1. *J Virol* 2003 November; 77(21):11767-80.

Kennedy G, Sugden B. EBNA1, a bifunctional transcriptional activator. *Mol Cell Biol* 2003 October; 23(19):6901-8.

Phiel C J, Zhang F, Huang E Y, Guenther M G, Lazar M A, Klein P S. Histone deacetylase is a direct target of valproic acid, a potent anticonvulsant, mood stabilizer, and teratogen. *J Biol Chem* 2001 Sep. 28; 276(39):36734-41.

Chen J, Ghazawi F M, Bakkar W, Li Q. Valproic acid and butyrate induce apoptosis in human cancer cells through inhibition of gene expression of Akt/protein kinase B. *Mol Cancer* 2006; 5:71.

Sheng Z, Liang Y, Lin C Y, Comai L, Chirico W J. Direct regulation of rRNA transcription by fibroblast growth factor 2. *Mol Cell Biol* 2005 November; 25(21):9419-26.

Kishida T, Asada H, Kubo K, Sato Y T, Shin-Ya M, Imanishi J, Yoshikawa K, Mazda O. Pleiotrophic functions of Epstein-Barr virus nuclear antigen-1 (EBNA1) and oriP differentially contribute to the efficacy of transfection/expression of exogenous gene in mammalian cells. *Journal of Biotechnology* 2007.

Ettehadieh E, Wong-Madden S, Aldrich T, Lane K, Morris A E. Over-expression of protein kinase Bα enhances recombinant protein expression in transient systems. *Cytotechnology* 2002; 38:11-14.

Krysan P J, Calos M P. Epstein-Barr virus-based vectors that replicate in rodent cells. *Gene* 1993; 137-143.

Tomiyasu K, Satoh E, Oda Y, Nishizaki K, Kondo M, Imanishi J, Mazda O. Gene transfer in vivo and in vitro with Epstein-Barr virus-based episomal vector results in markedly high transient expression in rodent cells. *Biochem Biophys Res Comm* 1998; 253: 733-738.

Goepfert U, Kopetzki E. Protein expression in rodent cells. International Patent Publication WO 2007/048601 published 3 May 2007.

Sunstrom N A, Kunaparaju R. Rodent expression system utilising polyoma virus and Epstein-Barr virus sequences. International Patent Publication WO 2005/024030 published 17 Mar. 2005.

Durocher Y, Perret S, Pham P L, St-Laurent G, Kamen A. Enhanced production of recombinant proteins by transient transfection of suspension-growing mammalian cells. International Patent Publication WO 2002/090533 published 14 Nov. 2002.

Durocher Y. Expression vectors for enhanced transient gene expression and mammalian cells expressing them. International Patent Publication WO 2006/096989 published 21 Sep. 2006.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. An expression system comprising one vector having an Epstein-Barr virus (EBV) nuclear antigen-1 (EBNA1) nucleotide sequence, a promoter and a polyadenylation signal for the EBNA1 nucleotide sequence, an EBV oriP nucleotide sequence, a gene of interest and a promoter and a polyadenylation signal for the gene of interest, wherein the expression system is integrated into a host genome and the gene of interest is stably expressed in a Chinese Hamster Ovary (CHO) cell.

2. The expression system of claim 1, wherein the EBNA1 nucleotide sequence encodes a truncated EBNA1 protein.

3. The expression system of claim 1, wherein the EBNA1 nucleotide sequence is codon-optimized.

4. A method of stably expressing a gene of interest in mammalian cells, the method comprising: transfecting a mammalian cell with an expression system as defined in claim 1; and, replicating the cell to provide mammalian cells that stably express the gene of interest.

5. An expression system comprising: a first vector having an Epstein-Barr virus nuclear antigen-1 (EBNA1) nucleotide sequence, a promoter and a polyadenylation signal for the EBNA1 nucleotide sequence; and, a second vector having a gene of interest, a promoter and a polyadenylation signal for the gene of interest, and an EBV oriP nucleotide sequence, wherein the expression system is integrated into a host genome and the gene of interest is stably expressed in a Chinese Hamster Ovary (CHO) cell.

6. The expression system of claim 5, wherein the EBNA1 nucleotide sequence encodes a truncated EBNA1 protein.

7. The expression system of claim 5, wherein the EBNA1 nucleotide sequence is codon-optimized.

8. A method of expressing a gene of interest in mammalian cells, the method comprising: transfecting a mammalian cell with an expression system as defined in claim 5; and, replicating the cell to provide CHO cells that stably express the gene of interest.

9. The method according to claim 8, wherein transfecting the cell with the first and second vectors is accomplished simultaneously, or the cell is transfected by one of the vectors first to produce a clone followed by transfection with the other vector to produce a clone that expresses the gene of interest.

10. The expression system according to claim 1, wherein the truncated EBNA1 protein comprises SEQ ID NO:2, SEQ ID NO:3, SEQ ID NO:4, SEQ ID NO:11, or SEQ ID NO:12.

11. The expression system according to claim 1, wherein the oriP nucleotide sequence comprises SEQ ID NO:9 or SEQ ID NO:10.

12. The expression system according to claim 5, wherein the first vector further comprises an oriP nucleotide sequence.

13. The expression system according to claim 5, wherein the truncated EBNA1 protein comprises SEQ ID NO:2, SEQ ID NO:3, SEQ ID NO:4, SEQ ID NO:11, or SEQ ID NO:12.

14. The expression system according to claim 5, wherein the oriP nucleotide sequences in the first and second vectors independently comprise SEQ ID NO:9 or SEQ ID NO:10.

* * * * *